US005976466A

United States Patent [19]
Ratner et al.

[11] Patent Number: 5,976,466
[45] Date of Patent: Nov. 2, 1999

[54] MULTIPLE-PROBE DIAGNOSTIC SENSOR

[75] Inventors: Buddy D. Ratner; James E. Francese, both of Seattle, Wash.

[73] Assignee: The Board of Regents of the University of Washington, Seattle, Wash.

[21] Appl. No.: 07/869,899

[22] Filed: Apr. 15, 1992

Related U.S. Application Data

[63] Continuation of application No. 07/397,778, Aug. 21, 1989, abandoned.

[51] Int. Cl.⁶ .................................................... G01N 33/48
[52] U.S. Cl. .......................... 422/82.11; 422/52; 436/86; 436/172; 250/361 C; 250/461.1; 385/130
[58] Field of Search ............................ 436/86, 149, 151, 436/172; 422/52–53, 62, 68.1, 82.05, 82.11; 250/361 C, 461.1; 385/130

[56] References Cited

U.S. PATENT DOCUMENTS 4,591,550   5/1986   Hafeman et al. .

OTHER PUBLICATIONS

Ives et al., "Protein Adsoprtion on the Surface of a Thin–Film Polymer Integrated Optical Wveguide", *Applied Spectroscopy*, 42:68–72 (1988).

Jellum et al., "Classification of Human Cancer Cells by Means of Capillary Gas Chromatography and Pattern Recognition Analysis", *Journal of Chromatography*, 217:231–237 (1981).

Merritt et al., Use of an Enzyme Linked Immunosorbent Assay (ELISA) for Quantification of Proteins on bthe Surface of Materials, *Journal of Biomeical Materials Research*, 22:99–109 (1988).

Williams, et al., "The Spatial Resolution of Protein Adsorption on Surfaces of Heterogeneous Metallic Biomaterials", *Journal of Biomedical Materials Research*, 23–339–350 (1989).

Muramatsu et al., "Piezoelectric Cyrstal Biosensor Modified with Protein A for Determination of Immunoglobulins", *Analytical Chemistry*, 59:2760–2763 (1987).

Absolom et al., "Protein Adsoprtion to Polymer Particles: Role of Surface Properties", *Journal of Biomedical Materials Research*, 21:161–171 (1987).

Carey et al., "Multicomponent Analysis Using an Array of Piezoelectric Crystal Sensors", *Analytical Chemistry*, 59:1529–1534 (1987).

Ballantine et al., "Correlation of Surface Acoustic Wave Device Coating Responses with Solubility Properties and Chemical Structure Using Pattern Recognition", *Analytical Chemistry*, 58:3058–3066 (1986).

Wenzel et al., "A Multisensor Employing an Ultrasonic Lamb–Wave Oscillator", *IEEE Transactions on Electron Devices*, 35:735–743 (1988).

Yeh et al., "Blood Compatibility of Surfaces Modified by Plasma Polymerization", *Journal of Biomedical Materials Research* 22:795–818 (1988).

Wolfbeis, "Fibre–Optic Sensors in Biomedical Sciences", *Pure and Applied Chemistry*, 59:663–672 (1987).

Roederer et al., "Microgravimetric Immunoassay with Piezoelectric Crystals", *Analytical Chemistry*, 55:2333–2336 (1983).

*Primary Examiner*—Lyle A. Alexander
*Attorney, Agent, or Firm*—Seed and Berry LLP

[57]        ABSTRACT

There is disclosed a diagnostic sensor device comprising a plurality of sensor probes, a detection device, and a computer for analyzing the signals generated from each sensor probe by multivariate statistical analysis. The plurality of sensor probes comprise a substrate that allows transmission of a signal and a partially selective surface coating the substrate wherein the partially selective surface binds proteins from a biological fluid by multiple, noncovalent interactions, and with the proviso that the partially selective surfaces of each sensor probe in the diagnostic sensor device be different. The diagnostic sensor device can be used as a method for diagnosing disease states in humans and animals, wherein the disease states are characterized by altered protein character and behavior of a biological fluid.

16 Claims, 15 Drawing Sheets

Relationship Between PRESS and the Number of Latent Variables in the PLS Model

Sensor probe loadings into the three latent variables

Single Bulk Acoustic Wave Device

ARRAY

SAW Device

Lamb Wave Device

Chemiresistor Device

MULTIPLE-PROBE DIAGNOSTIC SENSOR

CROSS-REFERENCE TO RELATED APPLICATION

This application is a continuation of U.S. Ser. No. 07/397,778 filed Aug. 21, 1989, now abandoned.

TECHNICAL FIELD OF THE INVENTION

The present invention relates to a diagnostic sensor device for assaying nonspecific protein adsorption from a biological fluid. The device is used for purposes of medical or veterinary diagnosis and for analysis of biological fluids. The device may also be used for chemical analysis of an analyte in a biological fluid. The invention utilizes an array of surfaces with different surface characteristics that adsorb proteins and other molecules in a partially selective fashion. The signal output from the array is analyzed by multi-variate statistical analysis. The analyzed data is related to a data matrix to determine a disease state, a physiological condition, or a quantity of analyte.

BACKGROUND OF THE INVENTION

The field of biosensors is an active research area. A sensor probe can be dipped into a biological fluid to measure the presence and/or concentration of an analyte, such as protein, a particular molecule, or a group of molecules. Biosensors generally have two principal components, a molecular-recognition element and a transducing or signal-generating element. Two common problems associated with biomedical sensing technology are the need for high specificity and the susceptibility of the sensing devices to fouling. Moreover, many of the current sensing devices are designed to detect only one or a small number of analytes or physiological conditions.

The molecular-recognition element is often not specific enough for the particular molecule or group of molecules (analytes) of interest and the molecular-recognition element can often cross-react with other molecules, causing a detection error.

Biofouling is the nonspecific adsorption and adhesion of biomolecules to a surface. When a biosensor is contacted with a biological fluid, biofouling is inevitable. In some sensing configurations, the biofouling is severe enough to render the device inoperable. Therefore, there is a need in the art for a signal-generating surface that, rather than trying to prevent biofouling, takes a reading based on the amount of nonspecific biomolecule adsorption, such as protein adsorption.

Biosensors have used a variety of detection devices in an attempt to quantitate the signal produced from the signal-generating system and the molecular-recognition element.

A common molecular-recognition element is an antibody, preferably a monoclonal antibody. In principle, antibodies are ideal candidates to use as molecular-recognition elements in biosensor design. Antibodies have the ability to bind antigens quite selectively and with binding constants (which indicate the ability of an antigen to interact with an antibody) that are neither too high nor too low. Antibodies can now be raised to react and bind specifically to numerous biomolecules, drugs, viruses, and cellular materials. However, because of the relatively high molecular weight of antibodies as compared with antigens, it is often difficult to couple an antibody-antigen binding reaction to a transducer in such a manner that the observed signal reflects an antibody-antigen interaction in a quantitative manner. Much of the biosensor art involves optimizing the union of the molecular recognition elements with the transducing or signal-generating elements.

One approach has been to coat piezoelectric crystals with antibodies to make biosensors for gaseous pollutants, such as the pesticide parathion. In the case of parathion, anti-parathion antibodies are coated on quartz piezoelectric crystals using bovine serum albumin/glutaraldehyde for immobilization. When mounted on a suitable apparatus, the piezoelectric crystals undergo changes in frequency if exposed to the antigen parathion. Such a biosensor may be sensitive in the parts-per-billion range.

It is also possible to use a fiber optic immunosensor with antibodies coating a fiber optic cable and detection by means of internal reflection spectroscopy. The interaction of the antibody coated on the fiber optic cable with its antigen can be monitored optically on a microscale. Such a biosensor has been used to measure concentrations of the drug methotrexate.

Immunoreaction biosensors have been coupled to electrochemical transducers. The antibodies are immobilized on a cellulose acetate membrane, and potential changes occur when the antigen-positive serum is added to the sample.

Piezoelectric systems are based upon a variation in the propagation speed of acoustic waves at the surface or in the bulk of a piezoelectric material, such as a quartz crystal. The variation is due to mass changes in the biomolecules bound to the coated layer. Immunological systems based upon a monoclonal IgG system have used a SAW (surface acoustic wave) technique. Results have been obtained with a detection limit as low as 1 ng. However, such measurements have suffered from buffer influence, drift, and calibration difficulties.

Another type of sensor measures the changes in capacitance due to changes in the dielectric constant caused by antibody-antigen interaction. An example of a biosensor consists of interdigitated copper electrodes on a glass surface, and insulated by a layer of parylene, and covered by a silicon monoxide film. An aminosilane allows a hapten to be fixed on the surface of the silicon monoxide. The addition of a solution containing antibodies induces a decrease in the capacitance. This is because of the variation of the dielectric constant under the membrane due to the binding of antibodies to the surface-bound antigen (hapten). Thus, the binding of the antigen or the antibody induces a variation of the heterostructure capacitance. Any variation of the surface potential leads to a shift in the capacitance-versus-voltage curve in the inversion range. The increase in the thickness of the dielectric layer induces a capacitance decrease in the accumulation range, which can be directly related to the size of the immobilized biomolecules and to the quantity of the titrated antigen.

Outside the field of biosensors, specific chemical sensors have been used to detect specific chemicals using pattern-recognition analysis of data from a sensor array. A chemical sensor array has sensors coated with different absorptive chemicals. The sensitivity and specificity of each of the absorption surfaces may vary. The data are collected in several channels of unique information provided by the array. The pattern recognition results recognize groups of chemicals through uniqueness of the patterns. Pattern recognition, as applied to a chemical sensor, requires: 1) that the analyte and the instrument's response are related; 2) that the analyte can be adequately represented as a set of sensor responses; 3) that a relationship can be discovered between various analytes and their responses by applying pattern-recognition methods; and 4) that the relationship can be extrapolated to other analytes in similar classes. There is a need in the art to use pattern recognition techniques in the field of biosensors, and especially for biosensors that have non-specific interactions.

In summary, the field of biosensors has focused on the ability to increase the specificity of the sensor and its sensitivity to the analyte. Both goals are difficult to achieve in a biological fluid. Accordingly, there is a need in the art for a sensor-type device which tries not to achieve selectivity or sensitivity, but instead can identify a variety of nonspecific molecules or physiological conditions while not requiring high specificity.

SUMMARY OF THE INVENTION

The present invention is based upon the theory that, in a disease state or a particular physiological condition, the composition and behavior of proteins in a patient's biological fluid will be altered. Evidence for the theory comes from the fact that the quantity and character of immunoglobulins change during disease states or physiological conditions and that some specific proteins may only be present or present in larger or smaller concentrations in a particular disease state (e.g., elevated IgE in allergic disease), or a physiological condition (e.g., human chorionic gonadotropin (HCG) in pregnancy). By characterizing protein behavior, one correlates data obtained from a protein-sensing mode to that disease state or physiological condition by multivariate statistical techniques. By obtaining data sets or matrices from many disease states, the sensor is calibrated, through the statistical program, to recognize a large number of physiological conditions or disease states. This database or matrix is used as a correlation model for patient diagnosis. Therefore, a multiple probe diagnostic sensor has the ability to detect a wide variety of disease states or physiological conditions with a single set of measurements.

Instead of pursuing the traditional means of biosensor development by attempting to increase the specificity of a biosensor array and the sensitivity of a biosensor array to certain analytes, the present invention applies pattern recognition to measurements of nonspecific interactions between biological molecules and an array of biosensors.

The diagnostic sensor device comprises a plurality of sensor probes, a detection device, and a means for analyzing the signals generated from each sensor probe. Each sensor probe has a partially selective surface that binds proteins. The diagnostic sensor device further comprises a means for generating a signal (i.e., one or a plurality of signal-generating devices), wherein the signal interacts with each sensor probe at the partially selective surface/protein interface, and a signal-collection device (detection device) or means for collecting the signals after interaction with the sensor probe. The specific signal used and the mode of signal interaction depend upon the specific means for interface analysis employed. Each sensor probe comprises a substrate that allows transmission of a signal and a partially selective surface, wherein the partially selective surface binds proteins from a biological fluid by multiple noncovalent interactions. The plurality of sensor probes have different partially selective surfaces on each sensor probe. The signal-generating device communicates with the partially selective surface of each sensor probe and generates a signal for each surface or probe.

The partially selective surface can be produced by a variety of techniques for altering the substrate surface. Examples of such techniques include methods for radio frequency plasma-polymerized film deposition, plasma-etching, spin casting, and metal-sputtering.

A radio frequency plasma polymerized film is produced by subjecting a feed material (monomer) to an electrical field oscillating at radio frequencies. Examples of plasma polymerized films include plasma-polymerized film from monomers, such as 2-Mercaptoethanol, allylamine, allyl alcohol, acrylic acid, methane, benzene, tetrafluoroethylene, methanol, acetone, chloroform, carbon tetrachloride, hexamethyl-disilane, ethyl sulfide, ethyl chloroformate, 1,1,1,3,3,3-Hexamethyldisilazane, acrylonitrile, pyridine, trimethyldiborane, tetramethylgermanium, 2-Chloropropane, formic acid, ethylene oxide, hexamethyldisiloxane, ferrocene, diphenyl selenide, butanone, bromobenzene, trimethyl borate, tetrahydrofuran, chlorotrimethylsilane, hydroxyethylmethacrylate, vinyltrimethylsilane, dimethyl sulfoxide, hexafluorobenzene, perfluoropropane, allene, other fluorocarbons, other chlorohydrocarbons, chlorofluorohydrocarbons and combinations thereof. The fluorocarbons, chlorohydrocarbons and chlorofluorohydrocarbons should be in the gaseous or liquid state and have carbon chain lengths no longer than twelve carbon atoms.

A plasma-etched surface can be produced by the radio frequency discharge in an atmosphere of, for example, air, argon, neon, nitrogen, diborane, phosphine, oxygen, fluorine, iodine, krypton, silicon (IV) chloride, sulfur dioxide and helium.

It is also possible to have a blend of an etchant and polymerizable species to incorporate the etchant gas or liquid into the polymeric film surface. Examples of etchant/polymerizable species blends, include, for example, oxygen/1,1,1,3,3, 3-Hexamethyldisilazane, nitrogen/ethyl sulfide, diborane/methane, phosphine/methane, diborane/tetrafluorethylene, oxygen/acetone, air/2-Chloropropane, iodine/diphenyl selenide, and silicon (IV) chloride/methane.

Spin-cast surfaces can be produced by dissolving a solid polymer in a solvent and pipetting the solution on a substrate while the substrate is revolving at high speed on a turntable. The solvent then evaporates, leaving a polymer film on the surface. Examples of spinscast films are poly (styrene), poly (urethane), and poly (ethyl methacrylate). An example of a solvent used for spin casting is 1,1,1,3,3,3-Hexafluoroisopropanol.

A metal-sputtered surface can be produced, for example, in a DC argon discharge with a metal target as the cathode. The substrate is placed in the vicinity of the discharge and becomes coated with a film of the target material. Examples of metal-sputtered surfaces are silver, gold and gold/palladium.

The substrate can comprise a variety of materials that allow transmission of the signal from the partially selective surface/biological fluid interface to the detection device. An example of a substrate material is a fiber optic cable.

It is important that the array of sensor devices each have sensor probes with different surface characteristics. The choice of surfaces for the array should allow for a wide range of surface characteristics, for example hydrophobic, hydrophilic, fluorinated, metallic, acidic, basic, anionic, cationic, phosphorous containing, silicon containing and combinations thereof. It is not necessary that each surface characteristic be represented in the array.

The detection device comprises a signal-collection device and can read any change in any characteristic of the partially selective surface/biological fluid interface. The detection device may send and receive signals, for example, via near-infrared spectroscopy, mid-infrared spectroscopy, visible spectroscopy, ultraviolet spectroscopy, surface acoustic wave (SAW) devices, bulk acoustic wave devices (commonly known as piezoelectric crystals), capacitance measurements, radioimmunoassay, fluorescence chemiluminescence, nuclear magnetic resonance, chemiresistors, electrochemical sensors, and enzyme-linked immunosorbent assay. The spectroscopy of varying wavelengths and fluorescence requires light sources for the signal-generating device.

BRIEF DESCRIPTION OF THE DRAWINGS

FIG. 4a shows that the first latent variables describe a linear relationship between the R and P data sets. FIG. 4b shows that the second latent variables describe a linear relationship between the R and P data sets.

FIG. 5 shows that Fb had a strong contribution to the predictive ability of the first latent variable.

FIG. 7 shows a clustering of test solutions based on their concentrations of fibrinogen.

FIG. 8 illustrates that PCA (Principal Component Analysis) was successful at classifying the test solutions based on the amount of hemoglobin they contained. FIG. 9 is an expansion of the lower right hand portion of FIG. 8.

FIG. 10 shows that the responses from the UN, ACE, and MTH sensor probes were loaded nearly equally, while the ALAM and TFE sensor probe loadings were different. This indicates that redundant or nearly redundant information is being contributed by the UN, ACE, and MTH sensor probes to the first two latent variables. Thus, the X-block consists of only three significantly different sensor probes when using the first two latent variables.

FIGS. 12–18 are described in Examples 7–14.

DETAILED DESCRIPTION OF THE INVENTION

Figure 1:
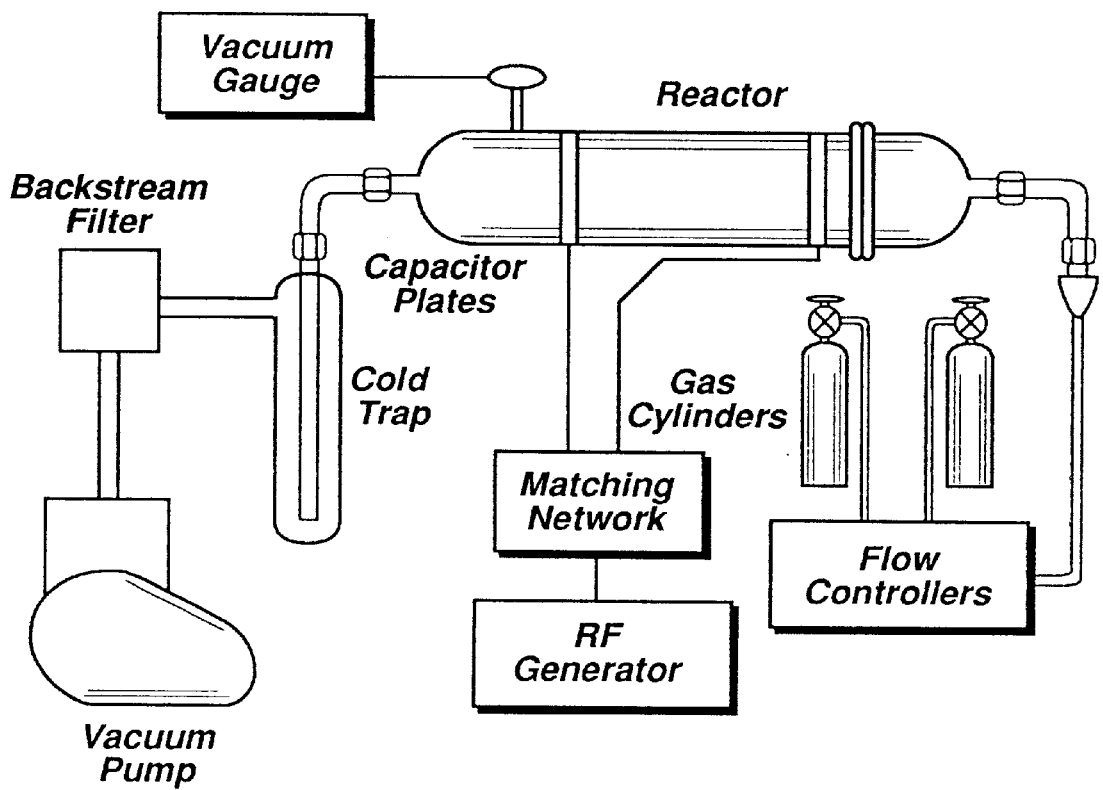
FIG. 1 illustrates a schematic of a plasma reactor system.
Figure 2:
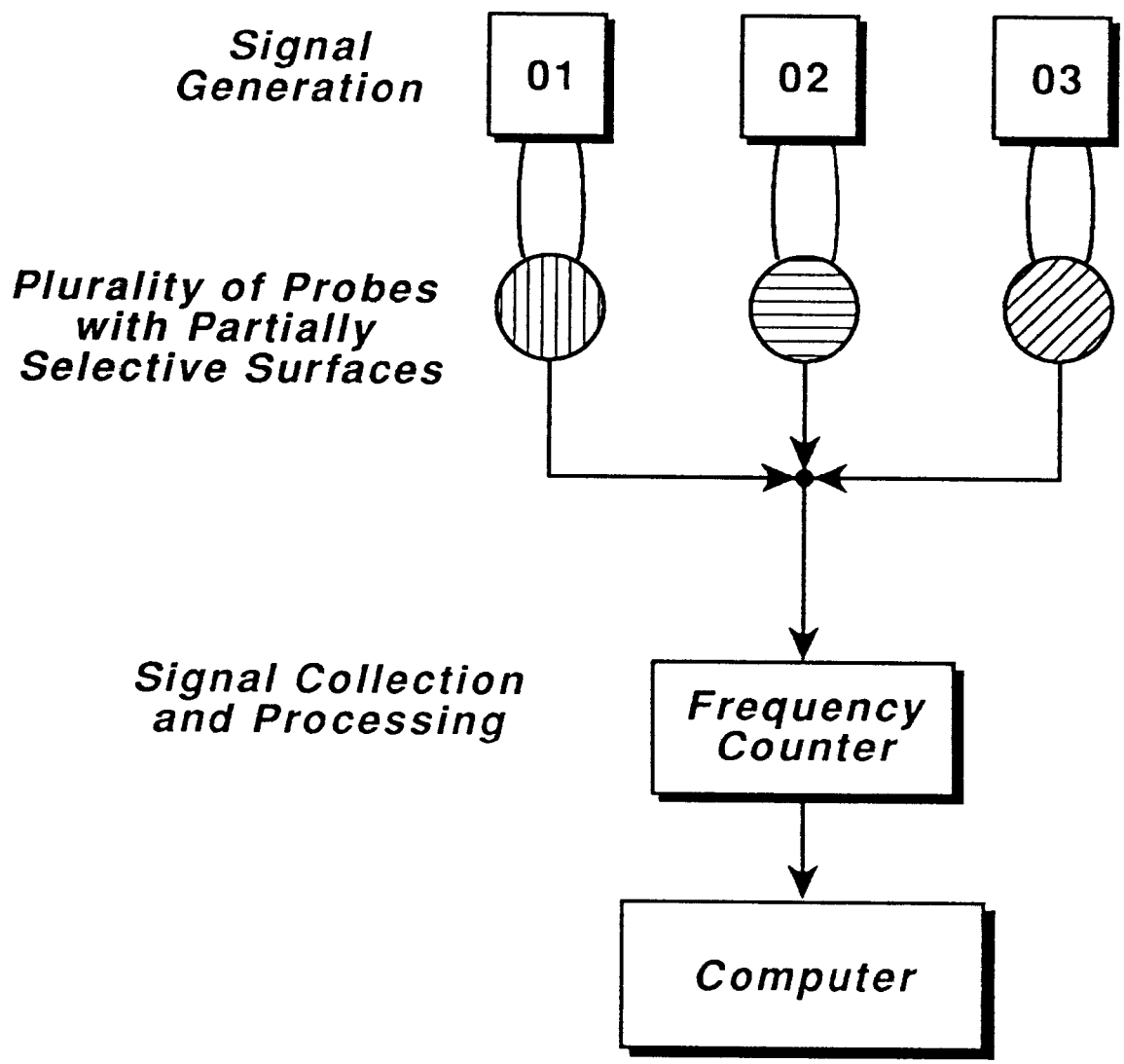
FIG. 2 illustrates a schematic diagram of one embodiment of the inventive diagnostic sensor device. The signal-generating devices are labeled as 01, 02, and 03 and comprise oscillator boards to induce crystal oscillation of the piezoelectric crystals attached to each oscillator board. Each sensor probe is a piezoelectric crystal with a different partially selective surface. Each piezoelectric crystal oscillates at a characteristic frequency, which is perturbed by protein absorption when the partially selective surface is in contact with a biological fluid. Each of the plurality of sensor probes communicates with a frequency counter that measures and displays the new (perturbed) oscillation frequency of each crystal. A computer receives the output over time of the frequency counter and collects and stores the data. After a sampling period (e.g., 10 minutes), the data is analyzed by multivariate statistical techniques.

In a disease state or in certain physiological condition for humans or animals, the composition and behavior of protein in a biological fluid, such as, whole blood, plasma, serum, tears, urine, saliva, sweat, semen, and bile, will be altered. The present invention characterizes the protein mixture and properties in biological fluid and then correlates the data obtained from the altered protein profile with a database or matrix obtained from the same protein sensing mode. This permits the protein profile to be related to a particular disease state or physiological condition. Unlike biosensors used to determine the concentration or presence of a particular analyte, the present invention senses the presence and behavior of proteins in a biological fluid and then statistically correlates this protein presence and behavior matrix to its database of protein presence and behaviors in specific disease states or physiological conditions. By obtaining data from many disease states or physiological conditions, the sensor is calibrated to recognize many different types of disease states or physiological conditions. This database is then used for diagnostic purposes. Therefore, the inventive multiple probe diagnostic sensor, coupled with a database of a plurality of disease states and physiological conditions, has the ability to detect a wide variety of disease states and physiological conditions with a single set of measurements.

The alteration of the composition and/or behavior of proteins is a known characteristic of many disease states and physiological conditions. The inventive device can diagnose disease states that have known altered protein concentrations such as an IgE elevation in allergic diseases. The inventive device can further function to diagnose diseases not characterized by an alteration of the concentration of a particular protein or directly causing the production of new proteins, such as diabetes. In the case of diabetes, the accompanying glucose concentration elevation will be manifested by altered protein adsorption data, thereby allowing the inventive device to make a diagnosis.

Other diseases cause ionic imbalances which will also be manifest by altered protein adsorption. As an illustration, the choice of saline buffer can affect protein adsorption in controlled laboratory experiments. Other examples of disease states having changed protein concentration and behavior include alpha lipoprotein often being decreased in chronic liver disease, and nephrosis often being characterized by increased levels of alpha-2-macroglobulin, β-lipoprotein and polymeric forms of haptoglobin.

The inventive device is further able to determine the concentration of an analyte in a biological fluid, for example, glucose. This is done by correlating the database with a specific component in the biological fluid when the specific component is, for example, glucose. The array of sensors can analyze the level of glucose in the biological fluid by correlating glucose levels with the protein adsorption profile.

The ability to correlate the data obtained from a specific measurement set with the database is accomplished by multivariate statistical techniques. Multivariate statistics are a collection of methods that can be applied to analyses when more than one measurement has been taken for each sample. Here, the diagnostic sensor device comprises a plurality of sensor probes which achieve a plurality of measurement parameters for each sample. Even the data obtained from a single sensor probe can provide many data points for multivariate statistical analysis. For example, an infrared (IR) spectrometer, as one example of a detection device, produces a spectrum that contains hundreds or thousands of data points, each of which contain information that may be of use. Multivariate statistical analysis will extract the useful information from even the subtle features of the spectrum which would ordinarily be overlooked. Equipped with commercially available software (e.g., ARTHUR™ from Infometrix, Seattle or Parvus™ from Elsevier), a computer can be taught to recognize the important features of complicated patterns, such a set of IR spectra. Once this calibration set has been established (i.e., the database is achieved), the multivariate statistical model can be used to predict the composition of unknown samples from its IR spectrum. For example, Haaland, "Quantitative Infrared Analysis For Borophosphosilicate Films Using Multivariate Statistical Methods," *Anal. Chem.* 60:1208–17 (1988), refers to a method to predict the boron and phosphorous content of borophosphosilicate glass.

Multivariate statistics include a variety of methods that can be loosely divided into two general groups: (1) pattern recognition, and (2) calibration and prediction. Each group contains a variety of different techniques. Both methods involve extraction of information from data sets having more than one measurement parameter for each sample. Pattern recognition is often used to classify (group) samples. However, pattern recognition does not calculate a numerical prediction for analyte concentrations. For example, one can classify shards of glass on the basis of which are "most alike" based on their elemental composition (i.e., boron-containing shards versus shards containing no boron). Discriminant analysis and principal component analysis are examples of pattern recognition techniques.

Calibration and prediction techniques are more quantitative. Using a data set of IR spectra from many samples, one can use calibration and prediction techniques to calculate "how much" boron the glass shards contain, and not only whether the shards contain any boron. This approach is described in Haaland, infra. Examples of calibration and prediction techniques include multiple linear regression and partial least squares.

The present invention uses multivariate statistical analysis to model protein adsorption behavior on a variety of different partially selective surfaces on a plurality of sensor probes. The present invention relies on the fact that protein adsorption to different partially selective surfaces varies markedly due to the different surface characteristics. This allows the construction of a diagnostic sensor device comprising a plurality of sensor probes wherein each sensor probe comprises a substrate that allows transmission of a signal and a partially selective surface, with the proviso that the partially selective surface of each sensor probe in the diagnostic sensor device is different. Therefore, the diagnostic sensor device, in essence, has each partially selective surface of each sensor probe partitioning protein solutions in a different fashion. Using multivariate statistical analysis, the model is built based upon a particular array of sensor probes wherein none of the specific sensor probes need to be selective for any given analyte or any specific protein. The detection from each sensor probe is based upon semiquantitative measurements, such as an IR spectrum of the surface. The correlation between the detection device signal and the concentration of particular analyte in a biological sample need not be linear. Further, it is not necessary to know, a priori, the correlation between the detection device signal and the particular analyte concentration or physiological condition.

It is important that the partially selective surface be able to adsorb proteins. It is not necessary that the protein adsorption be specific for certain proteins only that each surface produce reproducible results given the same or similar protein mixtures in the sample of biological fluid. For example, various factors such as surface tension, surface roughness, surface chemistry, and the ionic character of the surface are important parameters affecting a protein response to a given material. Preferably, radio frequency plasma deposition using different starting materials as monomers produces different surface chemistries in a convenient and reproducible manner.

Radio frequency plasma deposition is a process by which thin films (angstroms to microns in thickness) of gaseous or liquid feed materials are deposited on a substrate. The process is carried out in an evacuated reactor chamber, such as a Pyrex cylinder. An example of a typical plasma reactor is shown in FIG. 1. The feed materials (monomers) are bled into the reactor and subjected to an electrical field which is oscillating at radio frequencies. The starting material is broken apart into molecular fragments which deposit onto the surface of a substrate material placed in the reactor, forming a plasma polymerized film. Examples of monomers for radio frequency discharge polymers include methane, acetone, allylamine, acrylic acid, tetrafluoroethylene, 2-Mercaptoethanol, allyl alcohol, benzene, chloroform, other fluorocarbons up to twelve carbons in length, other chlorohydrocarbons up to twelve carbons in length and combinations thereof. Other monomers usable for plasma deposition include hexamethyldisilane, ethyl sulfide, ethyl chloroformate, 1,1,1,3,3,3,-Hexamethyldisilazane, acrylonitrile, pyridine, trimethyldiborane, acrylonitrile, pyridine, 2-Chloropropane, formic acid, ethylene oxide, ferrocene, diphenyl selenide, butanone, bromobenzene, trimethylborate, tetrahydrofuran, chlorotrimethylsilane, hydroxyethylmethacrylate, vinyltrimethylsilane, dimethyl sulfoxide, hexafluorobenzene, perfluoropropane, allene, other organometallics (e.g., tetramethylgermanium) and combinations thereof.

Examples of the plasma polymerized monomers that are used for a plurality of partially selective surfaces include methane for a hydrocarbon surface, acetone for a polar surface, allylamine for a nitrogen-rich surface, tetrafluoroethylene for a fluorine-rich surface, hexamethyldisilane for a Si-containing surface, ethyl sulfide for a sulfur-containing surface, 2-Chloropropane for a Cl-containing surface, ethylchloroformate for a Cl/O-containing surface, and 1,1,1,3,3,3-Hexamethyldisilazane for a Si/N-containing surface.

Plasma polymerization is an effective method for modifying substrate surfaces. Table 1, below, lists the surface elemental composition of polystyrene before and after modification with plasma films of methane, allylamine, acetone and tetrafluoroethylene. Elemental analysis was carried out by electron spectroscopy for chemical analysis (ESCA), a sensitive analytical tool to detect the presence and quantity of all surface elements except hydrogen or helium. Thus, Table 1 cannot list the hydrogen content of the surfaces.

diborane/tetrafluoroethylene, air/2-Chloropropane, iodine/diphenyl selenide, and silicon (IV) chloride/methane mixtures.

Spin-cast polymer surfaces can be produced by dissolving a solid polymer in a solvent and placing the solution on a substrate while the substrate is revolving at high speed on a turntable. This spreads the liquid polymer out evenly over the surface of the substrate. The solvent then evaporates, leaving a polymer film on the surface. Examples of spin-cast films are poly (styrene), poly (urethane), and poly (ethyl methacrylate). An example of a solvent used for spin-casting is 1,1,1,3,3,3-Hexafluoroisopropanol.

A metal-sputtered surface can be produced in a DC argon discharge with a metal target as the cathode. This discharge can be produced in an evacuated chamber into which argon has been introduced. The substrate material is also placed in the chamber. Argon is an etching gas, and impinges upon the metal target, knocking fragments from the metal surface. Fragments are transferred to the substrate material where they collect to form a thin film. Examples of metal-sputtered surfaces include substrates coated with a thin film of silver, gold, and gold/palladium. The elemental composition of the surface of a glass disk before and after gold-sputtering as measured by ESCA is given in Table 2, below. As before, the hydrogen content of the surfaces is not included.

TABLE 1

Surface Composition of Untreated Poly (styrene) and Poly (styrene) Coated with Various Radio Frequency Plasma Polymerized Films

| Monomer | Number of Samples | Elemental Composition, % | | | | | |
|---|---|---|---|---|---|---|---|
| | | C | O | N | F | S | Total |
| Untreated | 8 | 97.25 ± 1.03 | 2.75 ± 1.03 | 0.00 | 0.00 | 0.00 | 100.00 |
| Methane | 8 | 96.75 ± 0.54 | 3.27 ± 0.54 | 0.00 | 0.00 | 0.00 | 100.00 |
| Acetone | 9 | 89.21 ± 1.48 | 10.79 ± 1.48 | 0.00 | 0.00 | 0.00 | 100.00 |
| Allylamine | 9 | 77.32 ± 0.96 | 5.14 ± 0.68 | 17.08 ± 1.28 | 0.00 | 0.46 ± 0.40 | 100.00 |
| TFE | 7 | 42.02 ± 1.33 | 0.96 ± 0.31 | 0.46 ± 0.47 | 56.55 ± 1.51 | 0.00 | 100.00 |

Plasma etching is another method to produce partially selective surfaces. Some feed materials are non-polymerizable and will not form plasma-deposited films. The non-polymerizable materials, when subject to the reactor conditions, will form a cloud of energetic particles that impinge upon the substrate. The cloud of energetic particles will change the substrate's surface properties, including the affinity for proteins but will not deposit a film. This is known as a plasma-etched surface. For example, poly (ethylene) exposed to a plasma cloud of fluorine, $F_2$, will evidence fluorine incorporation upon spectral analysis but no film will be present. Other etching gases include, for example, argon, neon, helium, nitrogen, diborane, phosphine, oxygen, fluorine, iodine, krypton, silicon (IV) chloride, sulfur dioxide and air.

Etching and polymerizing gases can be combined to achieve other plasma modifications. For example, non-polymerizing gases can be incorporated into a plasma-deposited film by this method if presented together with a polymerizable gas. For example, poly (ethylene) exposed to a plasma consisting of a mixture of acetone (polymerizable) and nitrogen (etchant, non-polymerizable) will be covered with a deposited film after the reaction. However, the film will consist not only of carbon, hydrogen, and oxygen from the acetone, but will also contain nitrogen. Other examples of etchant/polymerizable species blends include oxygen/1,1,1,3,3,3-Hexamethyldisilazane, oxygen/acetone, ethyl sulfide/nitrogen, diborane/methane, phosphine/methane,

TABLE 2

Surface Composition of Untreated and Fold-Sputtered Glass Disks

| Sample | Elemental Composition, % | | | | | | |
|---|---|---|---|---|---|---|---|
| | C | O | Si | Na | Ti | Au | Total |
| Glass Disk | 13.96 | 56.43 | 26.34 | 2.92 | 0.34 | 0.00 | 100.00 |
| Gold-Sputtered Glass Disk | 35.34 | 0.00 | 0.00 | 0.00 | 0.00 | 64.66 | 100.00 |

A preferred embodiment of the inventive diagnostic device uses a thin film waveguide as a substrate, and a near-infrared spectrometer for signal generation. The partially selective surfaces are plasma films deposited in strips lengthwise on a base. Here, the substrate material (thin film waveguide) also forms the partially selective surface. The base (such as quartz) does not transmit signal. Electromagnetic radiation from the signal-generating device is coupled into a first prism using a single fiber optic cable. The signal detection device is a lead sulfide detector. Near-infrared radiation emitting from the second prism impinges upon the lead sulfide detector. The measured intensity at each wavelength is transferred to a computer (e.g., IBM 386 or clone thereof) and stored for subsequent data analysis.

The partially selective surfaces and substrates are plasma polymerized films from the following monomers:

allylamine, methane, acetone, tetrafluorethylene, hexamethyldisilane, ethyl sulfide and ethyl chloroformate. The computer uses multivariate statistical software using partial least squares (PLS) and principal component analysis (PCA). Two software programs are available including PCA Modeling Program version 1.0 ©1989, The Center for Process Analytical Chemistry, Department of Chemistry BG-10, University of Washington, Seattle, Wash. 98195, and PLS 2-Block Modeling version 3.1 ©1988, The Center for Process Analytical Chemistry, Dept. of Chemistry BG-10, University of Washington, Seattle, Wash. 98195.

The plurality of sensor probes is contacted with a patient sample. NIR (near-infrared), electromagnetic radiation of increasing wavelengths is coupled from the prism into the first partially selective surface, surface A (allyamine plasma film) at time t=1. The entire range of wavelengths is scanned, producing a spectrum of NIR radiation that has been perturbed by propagating through partially selective surface A and interacting with the proteins binding to partially selective surface A via multiple noncovalent interactions. At time t=2, NIR electromagnetic radiation of increasing wavelengths is coupled from the prism into partially selective surface B (methane plasma film). The entire range of wavelengths is again scanned. The procedure is repeated for each remaining, partially selective surface. At the completion of a scan for all surfaces, the cycle is repeated, because protein adsorption is a dynamic phenomenon (i.e., the adsorbed layer changes with time). The cycle is repeated approximately 10 times. The resulting data set is the intensity at each NIR wavelength for each partially selective surface for each cycle. This is an information-rich data set.

Any detection device that can generate a data point or data points from each sensor probe is appropriate to the present invention, so long as some of the data points generated reflect nonspecific protein adsorption at the partially selective surface/protein interface. Examples of appropriate detection devices and detection techniques include: infrared spectroscopy (near, mid, and far), surface acoustic wave devices, bulk acoustic wave devices, capacitance, radioimmunoassay, chemiluminescence, immunoassay, nuclear magnetic resonance, chemiresistor measurements, electrochemical sensors, Lamb-wave devices, fluorescence immunoassay, and enzyme-linked immunosorbent assay.

More particularly, chemiluminescence immunoassay uses an antibody or antigen bound to a chemiluminescent agent. That agent will emit light that can be measured by luminometry as the signal-collection device. The set of measurements will be luminescence produced versus time for each sensor probe.

It should be noted that many of the immunoassay techniques that use light-emitting sources, such as fluorescence and chemiluminescence, can be utilized with a fiber optic cable as a substrate that connects to the detection device. The substrate allows transmission of the signal to the detection device. The detection device determines the photon count from the partially selective surface/protein interface.

Piezoelectric crystals can be used as sensing devices with the present invention. A different partially selective surface is deposited on the surface of each piezoelectric crystal of an array forming a plurality of sensor probes. The resonant frequency of each crystal changes with time as proteins are adsorbed to the partially selective surface coating of each sensor probe. This matrix of frequency versus time measurements for each surface provides the data for analysis. A reference device is used to correct for system drift and variations due to temperature changes.

Similarly, surface acoustic wave (SAW) devices can measure a change in frequency versus time of a surface-propagating wave. Again, each SAW device has a different partially selective surface.

In another example, the capacitance measurements are determined when a partially selective surface coating is deposited directly on a capacitor surface. In this case, the capacitor becomes the substrate. As proteins are adsorbed to the surface, the capacitance changes with time. The matrix of capacitance changes with time for each surface becomes the data set for analysis by multivariate statistics.

In these and other modes, the time domain is an information-rich variable set that is exploited by the present invention. In many analytical techniques, the time data space is not efficiently utilized.

Near infrared spectroscopy (NIR), as a detection device, is an information-rich detection method and is the preferred detection device. Light of various wavelengths from an NIR spectrometer (signal-generating device) is coupled into plasma treated planar waveguides. When the partially selective surfaces on the substrate are contacted with a patient's sample of biological fluid, such as a blood sample, proteins will adsorb differently to each partially selective surface. By guiding light of various wavelengths into the planar waveguide, a near-infrared spectrum of the protein layer adsorbing to each partially selective surface is obtained. This method produces a large volume of data for the intensity as a function of time for each wavelength for each sensor probe. It is also possible to take the visible and ultraviolet spectrum of the protein depositing on the partially selective surface using different input wavelengths. The large volume of data will then be analyzed by multivariate statistical analysis.

The following examples are set forth for illustration purposes and are not designed to limit the broad aspects of the present invention.

EXAMPLE 1

This example illustrates a schematic of an inventive diagnostic sensor device comprising three piezoelectric crystals with different, partially selective surfaces. Each piezoelectric crystal with a partially selective surface is a sensor probe that is connected to an individual signal-generating device comprising an oscillator board that induces crystal oscillation. The piezoelectric crystal sensor probes oscillate at a characteristic frequency. The frequency of oscillation is perturbed by protein adsorption which occurs when the sensor probe is immersed in a biological fluid. Each sensor probe signal communicates by wire with a frequency counter, which is part of the signal-collection and processing system (i.e., signal-collecting device). The frequency counter measures and displays the new or perturbed oscillation frequency of each crystal or sensor probe. The data over time from the frequency counter is collected and stored in a microprocessor control device, such as a computer. After a sampling period of approximately 10 minutes, the data is analyzed by multivariate statistical techniques.

EXAMPLE 2

This example illustrates a diagnostic sensor device using an enzyme-linked immunosorbent assay (ELISA) as the detection technique. The plurality of sensor probes comprised a substrate material, poly (styrene) as a series of microtitre wells with different, partially selective surfaces. Four of the partially selective surfaces were plasma-deposited polymer films from the plasma-polymerized monomers methane (MTH), acetone (ACE), allylamine (ALAM), and tetrafluoroethylene (TFE). The chemical compositions of these plasma-deposited films are shown in Table 1 herein, including the untreated surface.

The untreated well was also suitable for use as a partially selective surface. The signal-generating device comprised an instrument that generated light of various wavelengths and projected the light through the test solutions that contacted the sensor probes. A built-in signal-collection device collected the transmitted light energy and measured its intensity.

The sensing device was used to analyze test solutions containing fibrinogen (Fb), albumin (Ab), and hemoglobin (Hb) in varying amounts in a citrate-phosphate buffer. Fibrinogen, albumin, and hemoglobin are physiologically important proteins. The plurality of sensor probes (i.e., microtitre wells with plasma-deposited polymer films or untreated) was contacted with the test solutions (i.e., biological fluid) for a total of two hours at approximately 35° C. The test solutions were removed by aspiration and the sensor probes were washed thoroughly with a surfactant solution containing 0.5% Tween 20 in a citrate-phosphate buffer. The amount of fibrinogen in the test solutions varied from 1.0 $\mu$g/ml to 25 $\mu$g/ml. This range of concentrations was divided into three categories: low concentrations (less than 8 $\mu$g/ml), intermediate concentrations (8 $\mu$g/ml to 16 $\mu$g/ml) and high concentrations (greater than 16 $\mu$g/ml). The amount of hemoglobin in test solutions varied from 10 $\mu$g/ml to 1000 $\mu$g/ml. This range of concentrations was divided into three categories: low concentrations (less than 300 $\mu$g/ml), intermediate concentrations (300 $\mu$g/ml to 600 $\mu$g/ml), and high concentrations (greater than 600 $\mu$g/ml). Albumin was present at a concentration varying from 20 $\mu$g/ml to 2000 $\mu$g/ml, with less than 600 $\mu$g/ml being low concentration, 600–1200 $\mu$g/ml being middle concentrations, and 1200–2000 $\mu$g/ml albumin being high concentrations.

A solution containing anti-fibrinogen, an antibody which has strong affinity for fibrinogen, was contacted with the sensor probes so the antibody could react with any fibrinogen noncovalently bound to the sensor probes. This particular antibody had been previously conjugated with the enzyme, horseradish peroxidase. The antibody was incubated with the sensor probes for two hours at approximately 35° C.

After the incubation the antibody solution was removed and the sensor probes were thoroughly washed with the surfactant solution. Next, the sensor probes were contacted with a solution containing the chromogenic horseradish peroxidase enzyme substrate, 3,3', 5,5'-tetramethylbenzidine and the oxidizing agent urea peroxide. The horseradish peroxidase enzyme catalyzes the reaction of the substrate to produce a colored product. The enzyme-substrate reaction was stopped after an incubation period of 35 minutes by the addition of 4N sulfuric acid. The amount of colored reaction product was qualitatively determined by measuring the amount of light transmitted through the solution in the microtitre well.

Forty test solutions of different compositions comprising fibrinogen, albumin, and hemoglobin were used. Each test solution contained all three proteins in varying amounts. The test solutions simulated alterations in the composition of the protein pool induced by a disease state as exemplified by the change in fibrinogen, albumin, and hemoglobin concentration amongst the differing test solutions. Table 3 below illustrates a portion of the test solution data.

TABLE 3

Sample Sensor Probe Response

| Solution | Sensor Probe Responses | | | | |
| --- | --- | --- | --- | --- | --- |
| | UN | ACE | MTH | ALAM | TFE |
| 1 | 0.257 | 0.504 | 0.120 | 0.654 | 0.890 |
| 2 | 0.116 | 0.433 | 0.072 | 0.019 | 0.386 |
| 3 | 0.308 | 0.952 | 0.185 | 0.622 | 1.025 |
| 4 | 0.997 | 1.298 | 1.068 | 0.536 | 1.163 |
| 5 | 0.068 | 0.232 | 0.053 | 0.799 | 0.703 |

The compositions of these test solutions were expressed as a forty-row by three-column (40×3) data matrix. The forty rows correspond to the number of unique test solutions, and the three columns contained the concentrations of fibrinogen, albumin, and hemoglobin in each test solution. The responses from the plurality of sensor probes were expressed by a forty-row by five-column (40×5) data matrix. The forty rows corresponded to the number of test solutions and the five columns contain measurements of the light transmitted through the substrate solution present in each partially selective sensor probe after the series of chemical reactions as described herein. Analysis of the multidimensional data set was optimized by utilizing multivariate statistical analysis.

We conducted a sample analysis of the data blocks to illustrate the effectiveness of multivariate statistical methods as a means to classify protein solutions and to predict analyte concentrations. The multivariate statistical methods are based on measurements of the noncovalent interactions of proteins with partially selective surfaces. The data were analyzed using the partial least squares algorithm (PLS), which is primarily a calibration and prediction technique, and by principal component analysis (PCA), which is primarily a pattern recognition technique. The ineffectiveness of traditional, univariate methods was shown by comparing the results given by the PLS algorithm to the results given by simple linear regression (SLR). These data demonstrate that the present invention has the potential to perform successfully in many clinical situations.

EXAMPLE 3

This example illustrates the calibration and prediction using partial least squares from the data achieved in Example 2. There were two steps in the partial least squares (PLS) modeling process. The first step (calibration) involved building the PLS model using known compositions of 27 of the 40 test solutions and the 27 sets of responses of the plurality of sensor probes to these test solutions. The 27 test solution compositions and sensor probe responses were termed the "calibration set". The known compositions were contained in a 27×3 (i×j) matrix "P" and the sensor probe responses were contained in a 27×5 (i×k) matrix "R". The second step (prediction) involved using the resulting PLS model to predict the concentrations of fibrinogen, albumin, and hemoglobin in the remaining 13 test solutions using the 13 sets of sensor probe responses to the 13 test solutions. The 13 test solutions and sensor probe responses were termed the "prediction set." The matrix of protein concentrations were considered to be the dependent data block (also called the Y-block) for computational purposes, and the matrix of sensor probe responses was considered to be the independent data block (also called the X-block).

Using partial least squares (PLS), the original data blocks, P and R, were re-expressed as latent variables. The latent variables were used to describe the variance of the original data blocks in a more concise fashion. Each column of the original matrix of sensor probe responses, R, was an axis in five dimensional space. Each row was a set of coordinates in five dimensional space defining the location of the sensor probe responses to each test solution. Using latent variables, this data set was re-expressed by defining a new set of axes, which are fewer in number than the original axes, to describe the variance that was relevant to changes in the compositions of the test solutions. The latent variables were mutually orthogonal, meaning that each latent variable was orthogonal to all the other latent variables.

Often, only the first few latent variables contained information relevant to calibration and prediction. Real data invariably contains noise and other information that is not relevant for representing the relationship between signal and analyte. PLS compresses the relevant information into the first few latent variables. Nonpredictive information is usually relegated to the later latent variables. Because a model can be built with only the first few latent variables, PLS provided an opportunity to largely rid the data of noise and variance not relevant to changes in protein concentration and construct smaller matrices for efficient prediction.

The PLS model consisted of a set of mathematical relationships between latent variables that described the variance in R and the latent variables that described the variance in P. The PLS algorithm iteratively uses information from the Y-block, the P matrix, when determining the latent variables of the X-block, the R matrix. The PLS algorithm iteratively uses information from the X-block, the R matrix, when determining the latent variables of the Y-block, the P matrix. In this way, the predictive ability of the model is optimized. The expressions used were:

$$R = TD + E \qquad \text{Eq. 1}$$

and $$P = UQ + G \qquad \text{Eq. 2}$$

where T was an i×h matrix containing the coordinates of the test solutions in a new space defined by the h latent variables associated with the matrix R. The maximum number of latent variables is equal to the number of columns in R, which is five. Thus, the maximum value of h is five. The i×h matrix U contained the coordinates of the test solutions in the new space defined by the h latent variables associated with the matrix P. The element of T and U were called the scores of R and P, respectively. The elements of h×k matrix D and h×j matrix Q were called the loadings, which described the relevance of the original variables (axes) in determining the latent variables (rotated axes). The h rows of D were the sensor probe response loadings vectors and the h rows of Q were the protein concentration loading vectors. The variance not modeled by PLS was contained in matrices E and G.

The latent variables in T were not optimal for describing the variance in the columns of R, but were rotated to also describe some of the variance in the columns of P. The latent variables in U were not optimal for describing the variance of the columns of P, but were rotated to also describe some of the variance in the columns of R. Each column of T (each X-block latent variable) was related to the corresponding column of U (each Y-block latent variable) by the following relationship:

$$u_h = t_h b_h + \epsilon \qquad \text{Eq. 3}$$

where $b_h$ were regression coefficients for the regression of R scores vector $t_h$ on P scores vector $u_h$, and the $\epsilon$ is the residual error. These expressions and the subsequent expressions where the subscript "h" is used are valid for each latent variable. For example, the value of "h" is one when the expression pertains to the first latent variable. The value of "h" is two when the expression pertains to the second latent variable and so on. The full relationship was:

$$U = TB + \Sigma \qquad \text{Eq. 4}$$

where B was an h×h diagonal matrix.

The latent variables were calculated one at a time in an iterative fashion. First, an estimate for the Y-block scores vector, $u_h$ an i×1 column vector, was made. It was estimated to be equal to the first column of the Y-block, $p_l$:

$$u_h = p_l \qquad \text{Eq. 5}$$

The X-block weights vector, $w_h^T$ (a 1×k row vector, proportional to the 1×k row loadings vector $d_h^T$), was then calculated:

$$w_h^T = u_h^T R / u_h^T u_h \qquad \text{Eq. 6}$$

The weights vector so obtained was then normalized to give it a length of one, resulting in a scaled 1×k weights vector $w_{h,s}^T$:

$$w_{h,s}^T = w_h^T / \|w_h^T\| \qquad \text{Eq. 7}$$

where $\|w_h^T\|$ was the norm of $w_h^T$. To calculate the norm of $w_h^T$, the individual elements of $w_h^T$ were squared and then added together. The norm was the square root of this sum.

The X-block scores vector $t_h$, an i×1 column vector, was then calculated:

$$t_h = R w_{h,s} / w_{h,s}^T w_{h,s} \qquad \text{Eq. 8}$$

The estimate for the Y-block scores vector $u_h$ was then revised. First, the loadings vector $q_h^T$, a 1×j row vector, was calculated and scaled, resulting in the scaled loadings vector $q_{h,s}^T$:

$$q_h^T = t_h^T p / t_h^T t_h \qquad \text{Eq. 9}$$

$$q_{h,s}^T = q_h^T / \|q_h^T\| \qquad \text{Eq. 10}$$

The new estimate for the Y-block scores vector $u_h$ was:

$$u_h = p q_{h,s} / q_{h,s}^T q_{h,s} \qquad \text{Eq. 11}$$

If the length of the new estimate for $u_h$ was more than one part per million different than the length of the previous estimate for $u_h$, the new estimate for $u_h$ was returned to Eq. 6 and the series of computations was repeated. This continued until the length of the new estimate for $u_h$ was less than one part per million different than the length of the estimate for $u_h$ from the previous iteration. The X-block loadings vector for this latent variable, $d_h^T$, was then determined:

$$d_h^T = t_h^T R / t_h^T t_h \qquad \text{Eq. 12}$$

The X-block loadings and scores vectors $d_h^T$ and $t_h^T$, and the weights vector, $w_h^T$, were normalized to give scaled vectors $d_{h,s}^T$, $t_{h,s}^T$, and $w_{h,s}^T$ and were saved for use in the prediction step.

The regression coefficient, $b_h$, for the relationship between the latent variables $t_h$ and $u_h$, was calculated:

$$b_h = u_h^T t_{h,s} / t_{h,s} \qquad \text{Eq. 13}$$

To insure that subsequent latent variable would be orthogonal to latent variable h, the variance described by latent variable h was subtracted from the R and P matrices:

$$R_h = R_{h-1} - t_{h,s} d_{h,s}^T \qquad \text{Eq. 14}$$

$$P_h = P_{h-1} - u_h q_{h,s}T \qquad \text{Eq. 15}$$

In this manner, all of the latent variables, equal to the number of columns in R, were calculated.

To optimize prediction using PLS, the optimum number of h latent variables was determined. The method used to do this was to look at the relationship between the number of latent variables and value of PRESS (Predictive Residual Error Sum of Squares).

PRESS was calculated by further dividing the 27 test solutions and associated sensor probe responses in matrices R and P of calibration data into two portions, a model-building set and a test set. The PLS model was initially built using the model-building set and one latent variable. The model was then used to predict the dependent values (protein concentrations) of the test set, for which the actual values were known. The value of PRESS, defined as the sum of the squared deviations of the predicted concentrations from the actual concentrations, was determined. A model using two latent variables was then constructed and used to predict the dependent values for the test set. The corresponding value of PRESS was calculated. This process was repeated for PLS models containing three, four, and five latent variables. Often, PRESS reached a minimum for a model containing less than the full number of possible latent variables. These later latent variables contained mostly variance not relevant to the prediction of test solution composition and noise. By leaving these latent variables out of the final model, the noise and nonrelevant variance was eliminated.

Figure 3:
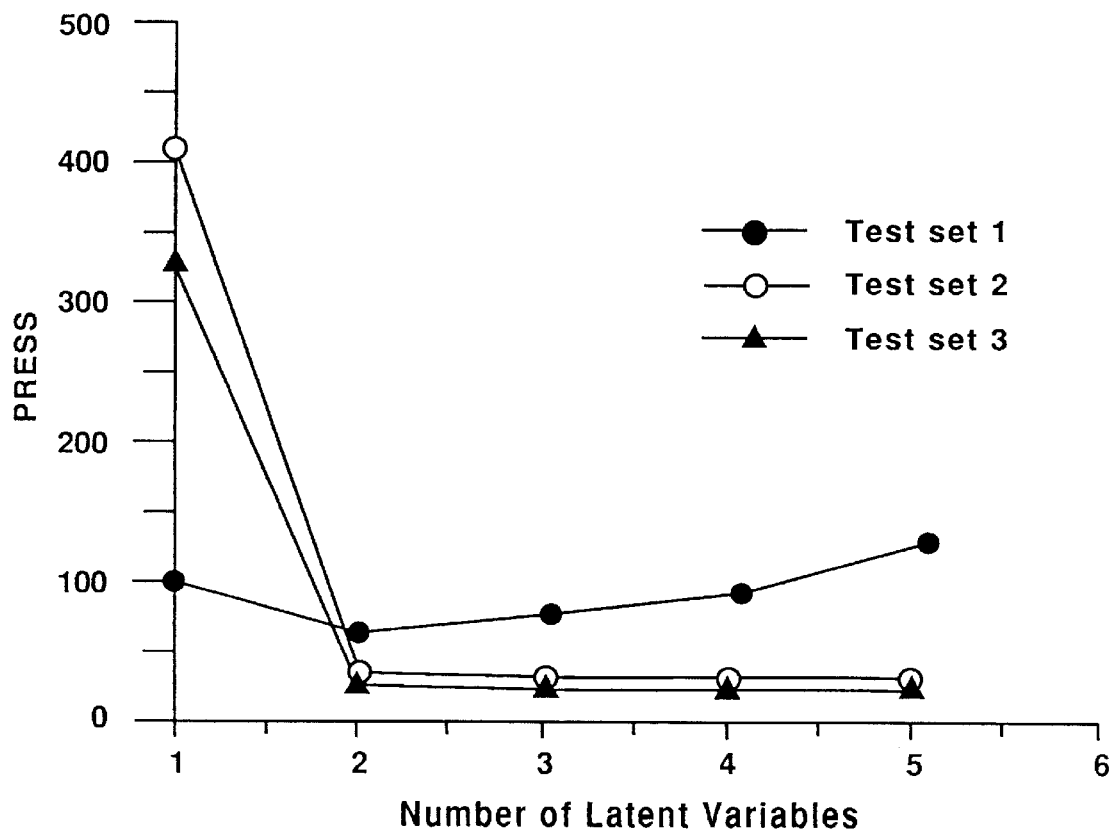
FIG. 3 illustrates the relationship between PRESS (Predictive Residual Error Sum of Squares) for the 27 test solution calibration set of sensor probe responses and protein concentrations when divided into the three test sets. The test solution data are explained in Example 2 herein.

FIG. 3 shows the results of PRESS calculations for a 27 test solution calibration set of sensor probe responses and protein concentrations which was split into three parts. Three models were constructed with two thirds of the data being used to predict the other third. This procedure was done three times, so that each test solution ended up as part of the test set at least once. A rule of thumb was that maximum predictive ability was attained for the model with the number of latent variables h corresponding to the minimum PRESS value.

After the h latent variables that best modeled the system had been chosen, the prediction of the set of 13×3 (n×j) protein concentrations (dependent variable block) was done using an 13×5 (n×k) matrix of sensor probe responses $R_u$ (independent variable block), where n was the number of test solutions for which predictions had to be made. The subscript "u" was used to designate that the responses in this block of independent variables were associated with test solutions whose compositions were "unknown" and had to be predicted by the model. The independent variable block $R_u$ was decomposed step by step, while the dependent variable block $p_p$, containing the predicted protein concentrations (thus the subscript "p") was built up.

First, a n×1 scores vector $t_u$ for the first latent variable was calculated using the independent block $R_u$ and the scaled weights and loadings from the calibration step. (In the following equations, the subscript "s" was omitted for simplicity):

$$t_{u,h} = R_{u,h-1} w_h \qquad \text{Eq. 16}$$

where k×1 column vector $w_h$ was the weights vector (similar to the k×1 loadings vector $d_h$) for latent variable h. The variance described by the h latent variable was then subtracted from the independent block:

$$R_{u,h} = R_{u,h-1} - t_{u,h} d_h^T \qquad \text{Eq. 17}$$

An estimate for the scores vector of the predicted protein concentrations was then obtained:

$$u_{u,h} = t_{u,h} b_h \qquad \text{Eq. 18}$$

The contribution of this latent variable to the prediction of the dependent block was:

$$P_{p,h} = u_{u,h} q_h^T \qquad \text{Eq. 19}$$

where $q_h^T$ was the loadings vector (a j×1 row vector) for the latent variable h. The above procedure was repeated for each of the h latent variables which had been retained in the model.

The entire predicted 13×3 $P_p$ matrix was the sum of all $P_{p,h}$ for the h latent variables retained in the model:

$$P_p = \Sigma P_{p,h} + P_{p,1} + P_{p,2} + P_{p,3} \qquad \text{Eq. 20}$$

Before PLS was performed, the data in the independent and dependent blocks were preprocessed by mean centering and then variance scaling. This required subtracting the column means from each column of R and then dividing the result by the standard deviation of that column. This was repeated for P.

The optimum number of latent variables was chosen based on the minimum in PRESS and by looking at plots of the latent variables. The PLS algorithm assumes a linear relationship between the scores contained in the X-block latent variables $t_h$ and the scores contained in the Y-block latent variables $u_h$. When an actual scores vs. scores plot of a certain latent variable reveals that this linear relationship is no longer true, then that part of the data consists mainly of other information not relevant to the modeling process or noise.

Figure 4A:
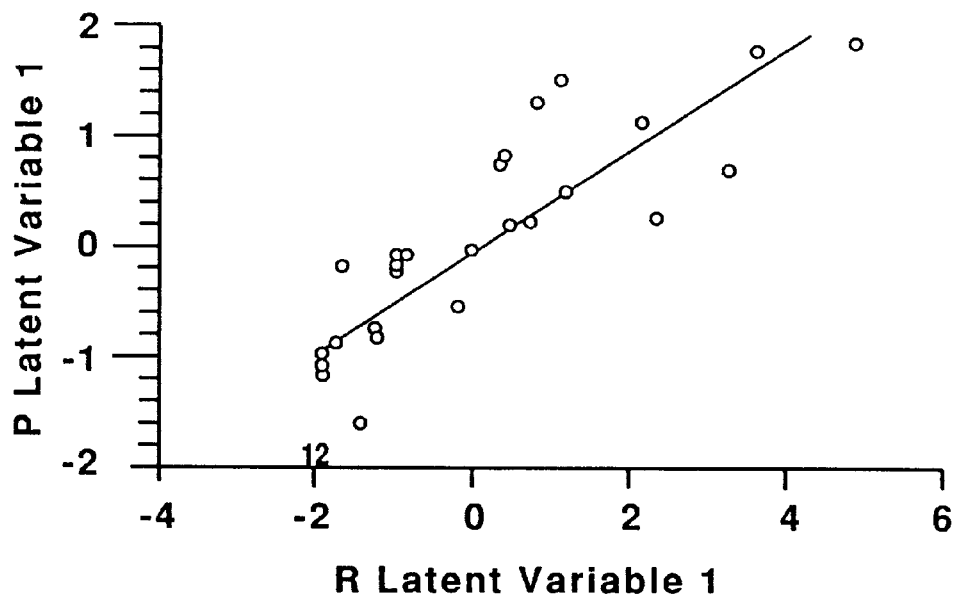
FIG. 4a shows the relationship between the first latent variable of the X-block and the first latent variable of the Y-block according to the data in Example 2 and the calculations in Example 3.

FIG. 4a shows the relationship between the first latent variable of the X-block and the first latent variable of the Y-block. The X-block scores ($t_h$) and Y-block scores ($u_h$) are shown along with the regression line between the two latent variables, as determined by the PLS model. The slope of this line is $b_1$, which was calculated during the calibration step of the PLS modeling. For example, the x-coordinate of test solution 12 on FIG. 4a is the twelfth element of the latent variable $t_l$, which is the first column of the X-block scores matrix T. It is evident from this plot that the first latent variable described a linear relationship between the R and P data sets.

Figure 4B:
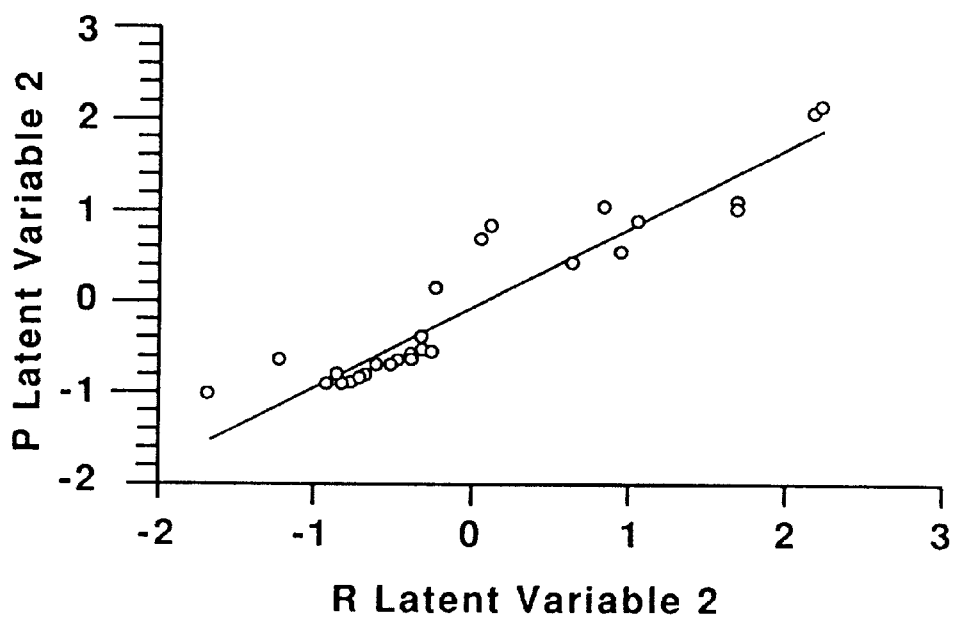
FIG. 4b shows the relationship between the second latent variable of the X-block and the second latent variable of the Y-block.

FIG. 4b shows the relationship between the second latent variable of the X-block and the second latent variable of the Y-block. The X-block scores ($t_h$) and Y-block scores ($u_h$) are shown along with the regression line between the two latent variables, as determined by the PLS model. The slope of this line is $b_2$, which was calculated during the calibration step of the PLS modeling. It is evident from this plot that the second latent variable also described a linear relationship between the R and P data sets.

Figure 5:
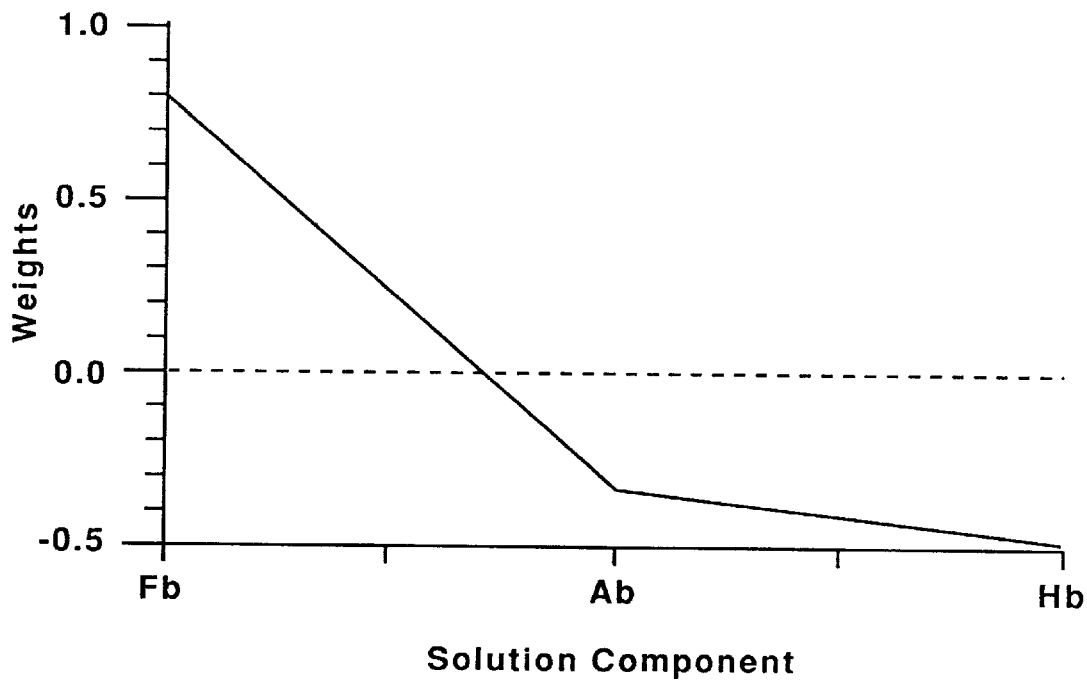
FIG. 5 illustrates the Y-block weights for the first latent variable according to the data in Example 2 and the calculations in Example 3. The weight of each original Y variable (Fb is fibrinogen, Ab is albumin, and Hb is hemoglobin) for Example 2 is a measure of how important that variable is in constructing a latent variable $u_h$. In other words.

The Y-block weights for the first latent variable are shown in FIG. 5. The weighting of each original Y variable (in this embodiment, the concentrations of fibrinogen, albumin, and hemoglobin) is a measure of how important that original variable was in construction a latent variable $u_h$. It is indicative of the original variable's contribution to the predictive ability of the latent variable. A high positive or high negative weight for an original Y variable shows that the original Y variable was important in contributing to the variance described by the latent variable. A weight near zero indicates a specific Y variable was unimportant in contributing to the variance described by the latent variable. This is important qualitative information. Fibrinogen was most strongly weighted in latent variable 1, while hemoglobin and albumin had lower weights. Albumin was the least important Y variable for determining the first Y-block latent variable.

Figure 6:
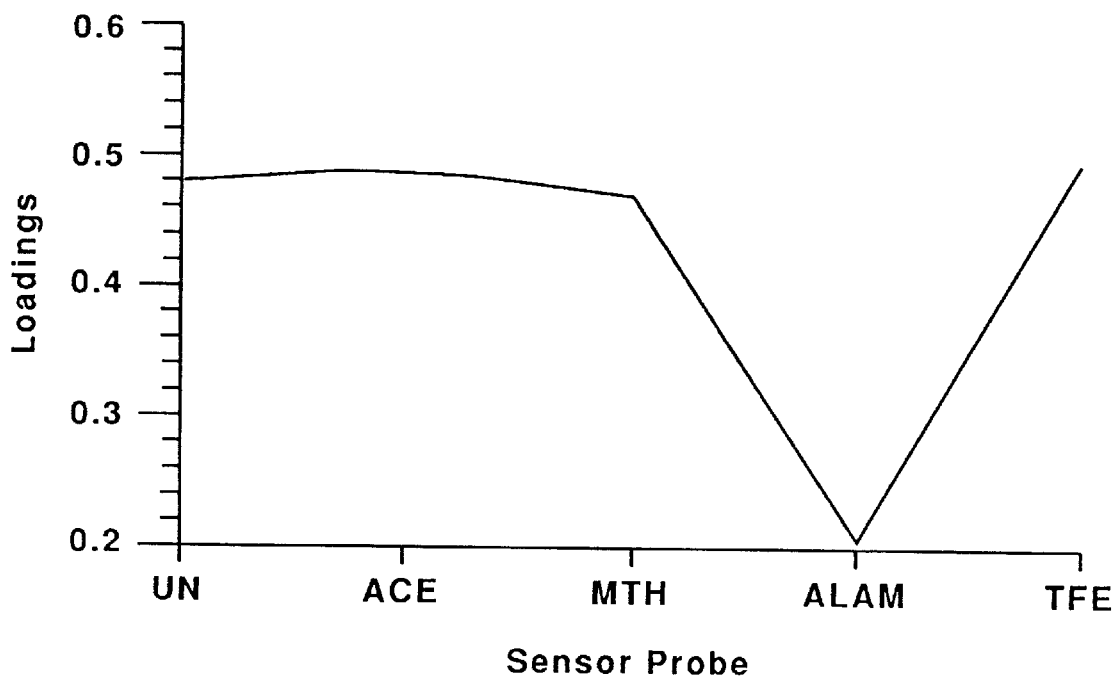
FIG. 6 illustrates the X-block loadings for the fist latent variable according to the data in Example 2 and the calculations of Example 3. The X-block loadings for the first latent variable indicate the relative importance of each original X variable toward contributing to the predictive ability of the latent variable. These data show that for the first latent variable, the loadings for the untreated sensor probe (UN), the acetone plasma-deposited film sensor probe (ACE), the methane plasma-deposited film sensor probe (MTH), and the tetrafluoroethylene plasma-deposited film sensor probe (TFE) were almost identical, while the allylamine plasma-deposited film sensor probe (ALAM) was loaded less strongly.

The X-block loadings for the first latent variable are shown in FIG. 6. The interpretation of these loadings is similar to the interpretation of Y-block weights. The loading of each original X variable is a measure of how important that original variable was in contributing to the predictive ability of the latent variable. This also is important qualitative information. For the first latent variable, the loadings for the untreated sensor probe (UN), the acetone plasma-deposited film sensor probe, (ACE), the methane plasma-deposited film sensor probe (MTH), and the tetrafluoroethylene plasma-deposited film sensor probe (TFE) were almost identical, while the allylamine plasma-deposited film sensor probe (ALAM) was loaded less strongly.

PLS models using either two or three latent variables were used to construct a model for predicting a 13×13 matrix $P_p$ of protein concentrations using as input the 13×5 matrix $R_u$ of sensor probe responses. The range of concentrations used for each protein and the PLS standard error of prediction (SEP) in predicting these concentrations using two latent variables is shown in Table 4. The SEP was calculated by:

$$SEP = (PRESS/d.f.)^{1/2} \qquad \text{Eq. 21}$$

where d.f., the degrees of freedom, was equal to the number of test solutions for which predictions were being made. For this PLS model, there were 13 degrees of freedom.

TABLE 4

Standard Error of Prediction (SEP) of PLS Model Used to Simultaneously Predict the Concentrations of Fb, Ab, and Hb

| Protein | Conc. Range in Test Solns. (µg/ml) | SEP (µg/ml) |
|---|---|---|
| Fibrinogen | 1.0–25.0 | 2.2 |
| Albumin | 20.0–2000.0 | 843.3 |
| Hemoglobin | 10.0–1000.0 | 264.7 |

The concentrations of fibrinogen were predicted quite accurately. The SEP was 2.3 µg/ml. The concentrations of hemoglobin were predicted less accurately; the SEP was 264.7 µg/ml (note: the concentration range was much larger). The concentrations of albumin could not be reliably predicted by this model.

Though PLS can be used to simultaneously predict the value of more than one Y variable, separate models can be built for the prediction of each individual Y variable. In each separate model, the latent variables are constructed to optimize the prediction ability of the model for that one Y variable. Increases in predictive power are sometimes realized by this practice. For example, information relevant to the prediction of fibrinogen concentrations may not be relevant for the prediction of hemoglobin concentrations. This nonrelevant information may actually interfere with the accuracy of hemoglobin predictions if the latent variables are constructed for the purpose of predicting the concentrations of both proteins. By building a model for the prediction of hemoglobin concentrations only, the latent variables can be optimized to contain information relevant to the prediction of hemoglobin concentrations. In a clinical situations, this would not increase the complexity of test solution analysis, for a computer can easily store various sets of model parameters. A user of the sensing device can select, perhaps from a screen menu, which set of parameters to use.

To build each model, the same matrix of 27×5 independent R values was used. The dependent block consisted of a 27×1 p vector containing the concentrations for only a single protein. The optimum number of latent variables was chosen. The resulting PLS model was used to predict a 13×1 $p_p$ vector using a 13×5 matrix of sensor probe responses $R_u$. This procedure was repeated so the concentration of each protein could be predicted by a separate PLS model. The SEP of the PLS predictions of the protein concentrations using these individual models is shown in Table 5. For these test solutions and sensor probe responses, the accuracy of the hemoglobin prediction was markedly improved by this procedure. This showed that forcing the PLS model to simultaneously predict the concentrations of fibrinogen, albumin, and hemoglobin interfered with the prediction of the hemoglobin concentrations.

TABLE 5

Standard Error of Prediction (SEP) of PLS Models Used to Individually Predict the Concentrations of Fb, Ab, and Hb

| Protein | Conc. Range in Test Solns. (µg/ml) | SEP (µg/ml) |
|---|---|---|
| Fibrinogen | 1.0–25.0 | 2.3 |
| Albumin | 20.0–2000.0 | 844.7 |
| Hemoglobin | 10.0–1000.0 | 194.2 |

By conventional, univariate means, even the reliable quantitation of a single analyte using ELISA can be difficult. Accordingly, the performance of this plurality of sensor probes was clearly superior to the conventional means of analysis, for it was able to accurately predict fibrinogen concentrations and also had some predictive ability for hemoglobin concentrations.

EXAMPLE 4

This example illustrates a comparison of multivariate versus univariate data analysis of the data from Example 2. The results obtained from PLS were compared to the results obtained using simple linear regression (SLR). SLR is a technique commonly employed in the calibration and prediction of immunoassay data. using SLR, a relationship between only one independent (x) variable (a single row of R) and only one dependent (y) variable (a single row of P) can be found. Thus, SLR is a univariate (one variable) technique. The model produced by SLR is a straight line, described by the expression y=mx+b, where m is the slope of the line and b is the y value at which the line intercepts the y axis.

Using SLR, a model was built to describe the relationship between the 27 sensor probe responses from the UN sensor probe and the 27 fibrinogen concentrations in the test solution calibration set used in the calibration step of the PLS modeling process. After the values of m and b had been determined, the model was used to predict the fibrinogen concentrations in the 13 test solutions from the prediction step of the PLS modeling process using the 13 corresponding responses from the UN sensor probe. Then, a SLR model was built to describe the relationship between the 27 sensor probe responses obtained from the UN sensor probe and the 27 hemoglobin concentrations in the test solution calibration set used in the calibration step of the PLS modeling process. After the values of m and b had been determined, the model was used to predict the hemoglobin concentrations in the 13 test solutions from the prediction step of the PLS modeling process using the 13 corresponding responses from the UN sensor probe. For this model and all SLR models, the 27 samples used to build the SLR model were the same ones used to build the PLS model in Example 3. The 13 samples used to test the predictive ability of the SLR model were the same as those used to build the PLS model.

Additional SLR models were built to describe the relationship between the 27 sensor probe responses from the ACE sensor probe and the 27 fibrinogen concentrations in the test solution calibration set and to describe to relationship between the 27 sensor probe responses from the ACE sensor probe and the 27 hemoglobin concentrations in the test solution calibration set. These models were then used to predict the concentrations of fibrinogen and hemoglobin in the 13 test solutions in the prediction set.

The procedure was repeated for the MTH, ALAM, and TFE sensor probes. Two SLR models were built from each set of sensor probe responses, one for the prediction of fibrinogen concentrations, and one for the prediction of hemoglobin concentrations.

The SEP for each of these SLR models is given in Table 6, along with the model parameters m and b. It can be seen that none of the individual sensor probes, used alone for prediction with SLR, performed as well as the plurality of sensor probes, modeled in tandem using PLS. Using PLS, the best SEP for the prediction of fibrinogen concentrations was 2.2 μg/mL (Table 4). Using PLS, the best SEP for prediction of hemoglobin concentrations was 194.2 μg/mL (Table 5).

TABLE 6

Prediction Accuracy Of SLR Models; Model Parameters m and b

| Sensor Probe | Protein | m | b | SEP |
|---|---|---|---|---|
| UN | fibrinogen | 14.3 | 6.0 | 9.0 |
| | hemoglobin | −758.7 | 505.5 | 258.0 |
| ACE | fibrinogen | 12.6 | 2.8 | 8.0 |
| | hemoglobin | −715.6 | 699.9 | 271.9 |
| MTH | fibrinogen | 17.2 | 9.3 | 9.3 |
| | hemoglobin | −779.5 | 475.1 | 269.8 |
| ALAM | fibrinogen | 27.5 | −0.6 | 4.5 |
| | hemoglobin | 612.0 | 127.3 | 308.0 |
| TFE | fibrinogen | 19.5 | −3.2 | 5.0 |
| | hemoglobin | −474.4 | 643.4 | 258.6 |

Based on the SEP of the two methods, we concluded that the PLS model performed better than SLR for the prediction of fibrinogen and hemoglobin concentrations. However, there was a possibility that the two SEPs given by the two methods were not different in a statistical sense, in which case that conclusion would be unfounded. To test the probability that our conclusion was unfounded, an F-test was conducted. The F-test used as input the F statistic and the degrees of freedom (d.f.) in the SLR and PLS data sets. In this case, the degrees of freedom was equal to 13, the number of test solutions for which dependent values were being predicted. The F statistic was calculated as follows:

$$F = [SEP^2(SLR)/d.f.(SLR)]/[SEP^2(PLS)/d.f.(PLS)] \quad \text{Eq. 22}$$

By convention, the larger SEP is placed in the numerator when calculating the F statistic. The output of the F-test was the alpha probability ($\alpha$), the probability that the SEPs given by the two methods were not statistically different and that our conclusion was unfounded. For the prediction of fibrinogen using the ALAM sensor probe, which had the best SEP using SLR, $\alpha = 0.0074$, meaning that there is only 0.74% chance that PLS did not perform better than SLR. For the prediction of hemoglobin using the UN sensor probe, which had the best SEP using SLR, $\alpha = 0.1590$. Thus, we can be 84% (100% −15.9%) sure that PLS performed better than the best SLR case for hemoglobin concentration prediction.

It should be noted that some of the SLR results were much worse than those used in the above analysis. Using the worst SLR results, $\alpha = 3.50 \times 10^{-6}$ for fibrinogen prediction (MTH sensor probe) and $\alpha = 0.054$ for hemoglobin prediction (ALAM sensor probe). In the likely event that the prediction errors are positively correlated between the PLS and SLR prediction methods, the calculated $\alpha$ would be conservative (Haaland, et al. *Anal. Chem.* 60:1193), and should actually be smaller. In this case, the chance that PLS performed better than SLR is actually greater than the probability determined by the F-test.

In many clinical situations, an actual numerical prediction for an analyte level is unnecessary. Diagnoses can often be made on the basis of whether the amounts of certain indicator species are below normal, in the normal range, or elevated above the normal range. This is a form of pattern recognition. The diagnostic sensor probe of Example 2 was tested in this capacity.

Using the Example 2 sensor probe responses for the forty test solutions, a cross-validation PLS procedure was done. This was a different type of modeling than that previously done with PLS. The cross-validation modeling procedure involved building forty different PLS models. Each time, 39 of the test solutions were used to build a model that was then used to predict the concentration of either fibrinogen or hemoglobin in the remaining test solution from the sensor responses to that test solution.

The amount of fibrinogen in the test solutions varied from 1 μg/ml to 25 μg/ml. This range of concentrations was divided into three categories: low concentrations (greater than 8 μg/ml), intermediate concentrations (8 μg/ml to 16 μg/ml), and high concentrations (greater than 16 μg/ml). The known concentrations in the forty test solutions were compared with the predicted concentrations from the PLS models. A perfect set of models would have placed all 40 of the predicted values in the same category as the actual known values. The present models placed 37 of the predicted values in the same category.

The amount of hemoglobin in the test solutions varied from 10 μg/ml to 1000 μg/ml. This range of concentrations was divided into three categories: low concentrations (less than 300 μg/ml), intermediate concentrations (300 μg/ml to 600 μg/ml), and high concentrations (greater than 600 μg/ml). The known concentrations in the forty test solutions were compared with the predicted concentrations from the PLS models. A perfect set of models would have placed all 40 of the predicted values in the same category as the actual known values. The present models placed 35 of the predicted values in the same category.

Accordingly, the fact that reliable information about hemoglobin concentrations can be obtained from an anti-fibrinogen assay demonstrates the usefulness of the present approach and illustrates how a plurality of sensor probes can extract knowledge from measurements of nonspecific protein interactions with partially selective surfaces. This represents a significant achievement in the art.

The superior performance of the diagnostic sensor probe of Example 2 over the previous attempts in the art to construct such a device was confirmed by comparing the PLS cross-validated models to correctly categorize test solutions to the ability of SLR cross-validated models to correctly categorize test solutions. Because of the inherent limitations of univariate techniques such as SLR, the responses from only a single sensor probe could be used to predict the concentration of only a single protein. Using the sensor probe responses for the forty test solutions, a cross-validation SLR procedure was done. This was different type of modeling than that previously done with SLR. The cross-validation modeling procedure involved building forty different SLR models. Each time, 39 of the test solutions were used to build a model that was then used to predict the concentration of either fibrinogen or hemoglobin in the remaining test solution from the sensor response to that test solution.

Using SLR, a cross-validated model was built to describe the relationship between the sensor probe responses obtained from the UN sensor probe and the fibrinogen concentrations in the 40 test solutions. This involved building forty different SLR models. Each time, 39 of the test solutions were used to build a model that was then used to predict the concentration of fibrinogen in the remaining test solution from the UN sensor response to that test solution. The SEP for the set of 40 predicted values was calculated as in Eq. 21, except that in this case there were 40 degrees of freedom. A cross-validated SLR model was then built to describe the relationship between the sensor probe responses obtained from the UN sensor probe and the hemoglobin concentrations in the 40 test solutions. This involved building forty different SLR models. Each time, 39 of the test solutions were used to build a model that was then used to predict the concentration of hemoglobin in the remaining test solution from the UN sensor response to that test solution. The SEP was calculated.

Cross-validated SLR models were also built using the responses from the ACE, MTH, ALAM, and TFE sensor probes to predict the concentrations of fibrinogen and then the concentrations of hemoglobin in the test solutions. The cross-validated model using the responses from the ALAM sensor probe resulted in the lowest SEP (4.60 $\mu$g/ml) for the prediction of the fibrinogen concentrations in the test solutions. Thirty-two of the 40 test solutions were categorized correctly by these most accurate SLR models according to the concentration of fibrinogen they contained. The PLS models were able to correctly categorize 37 of the 40 test solutions using the cross-validation method.

The cross-validated model using the responses from the ACE sensor probe resulted in the lowest SEP (324.7 $\mu$g/ml) for the prediction of the hemoglobin concentrations in the test solutions. Only 18 of the 40 test solutions were categorized correctly by the models according to the concentration of hemoglobin they contained. In contrast, the PLS models were able to correctly categorize 35 of the 40 test solutions.

EXAMPLE 5

This example illustrates a pattern recognition approach using principal component analysis using the data of Example 2. Principal component analysis (PCA) is a pattern recognition technique used to classify a set of analyzed samples. PCA defines axes in space that describe the major sources of variance in measurements taken on the samples, contained in a matrix of independent variables R. The new axes are called the principal components (PCs). The coordinates of the samples in the rotated space are called the scores. The spatial orientation of the analyzed samples can be examined visually using scores vs. scores plots in the two dimensional planes defined by the PCs. In these projections, clusters of samples often appear, indicating that these samples had a similar covariance for the measured variables and may be inherently similar in a chemical, physical, etc., sense.

Principal component analysis is a method that considers the independent variable block, the X-block, only. Information contained in the dependent variable block, the Y-block, is not considered. The independent variable block was the 40×5 (i×k) matrix R containing the responses of the plurality of sensor probes to the 40 test solutions containing varying amounts of fibrinogen, albumin, and hemoglobin. Before PCA was performed on the matrix R, the data in R was preprocessed by mean centering and then variance scaling. This required subtracting the column means from each column of R and then dividing the result by the standard deviation of that column.

The principal components were linear combinations of the original measured variables. The first principal component was the direction in the column space of R that described the maximum variation in sensor probe responses to the test solutions. The subsequent principal components described decreasing amount of the original variation in the test solutions.

The expression used was:

$$R = AZ + E \qquad \text{Eq. 23}$$

where A was an i×c matrix containing the coordinates of the test solutions in the new space defined by the c principal components. The elements of A were called the scores of R. The elements of the c×k matrix Z were called the loadings, which described the relevance of the original variables (axes) in determining the principal components (rotated axes). The c rows of Z were the sensor probe response loadings vectors. The variance not modeled by PCA was contained in the c×k matrix E.

The principal components were calculated one at a time in an iterative fashion. First, an estimate for the X-block scores vector, $a_c$ (an i×1 column vector), was made. It was estimated to be equal to the first column of the X-block, $r_1$:

$$a_c = r_1 \qquad \text{Eq. 24}$$

The X-block loadings vector, $z_c^T$, a 1×k row vector, was then calculated:

$$z_c^T = a_c^T R / a_c^T a_c \qquad \text{Eq. 25}$$

The loadings vector so obtained was then normalized to give it a length of one, resulting in the scaled 1×k weights vector $z_{c,s}^T$:

$$z_{c,s}^T = z_c^T / \|z_c^T\| \qquad \text{Eq. 26}$$

where $\|z_c^T\|$ was the norm of $z_c^T$. To calculate the norm of $z_c^T$, the individual elements of $z_c^T$ were squared and then added together. The norm was the square root of this sum.

The new estimate for the X-block scores vector (an i×1 column vector) $a_c$ was then obtained:

$$a_c = R z_{c,s} / z_{c,s}^T z_{c,s} \qquad \text{Eq. 27}$$

If the length of the new estimate for $a_c$ was more than one part per million different than the length of the previous estimate for $a_c$, the new estimate for $a_c$ was returned to Eq. 25 and the series of computations was repeated. This continued until the length of the estimate for $a_c$ was less than one part per million different than the length of the estimate of $a_c$ from the previous iteration.

To ensure that subsequent principal components would be orthogonal to principal component c, the variance described by principal component c was subtracted from the R matrix:

$$R_h = R_{h-1} - a_{h,s} z_{h,s}^T \qquad \text{Eq. 28}$$

In this manner, all of the principal components, equal to the number of columns in R, were calculated.

The amount of fibrinogen in the test solutions varied from 1 μg/ml to 25 μg/ml. Test solutions were assigned to categories based on their fibrinogen content: low concentrations (less than 8 μg/ml), intermediate concentrations (8 μg/ml to 16 μg/ml), and high concentrations (greater than 16 μg/ml). PCA was performed on the 40×5 data matrix R containing the responses from the plurality of sensor probes to each of the test solutions. Two dimensional projections of sensor probe responses to the test solutions on various principal components were examined to see if the test solutions were clustered according to the amount of fibrinogen they contained. In these plots, the axes are the principal components and the coordinates of the test solutions are the scores.

Figure 7:
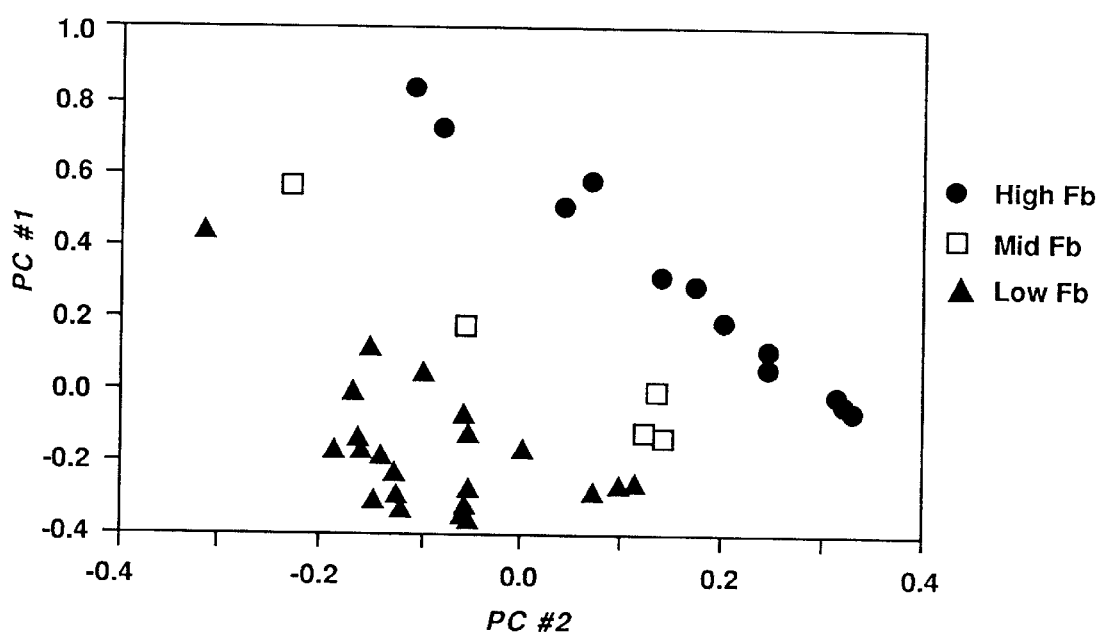
FIG. 7 illustrates two dimensional projections of the test solutions of Example 2 on the first two principal components of Example 5. The axes are the principal components (PC #1 or #2) and the coordinates of the test solutions are the scores.

FIG. 7 illustrates a scores vs. scores plot for the first two principal components. It can be clearly seen that there was a clustering of test solutions based on their concentration of fibrinogen. PCA defined regions in this two dimensional space in which test solutions containing low, intermediate, or high concentrations of fibrinogen were exclusively located. Other test solutions, when projected onto this two dimensional plane (the procedure for this will be described shortly), should fall into one of these three regions, determined by their fibrinogen content.

Figure 8:
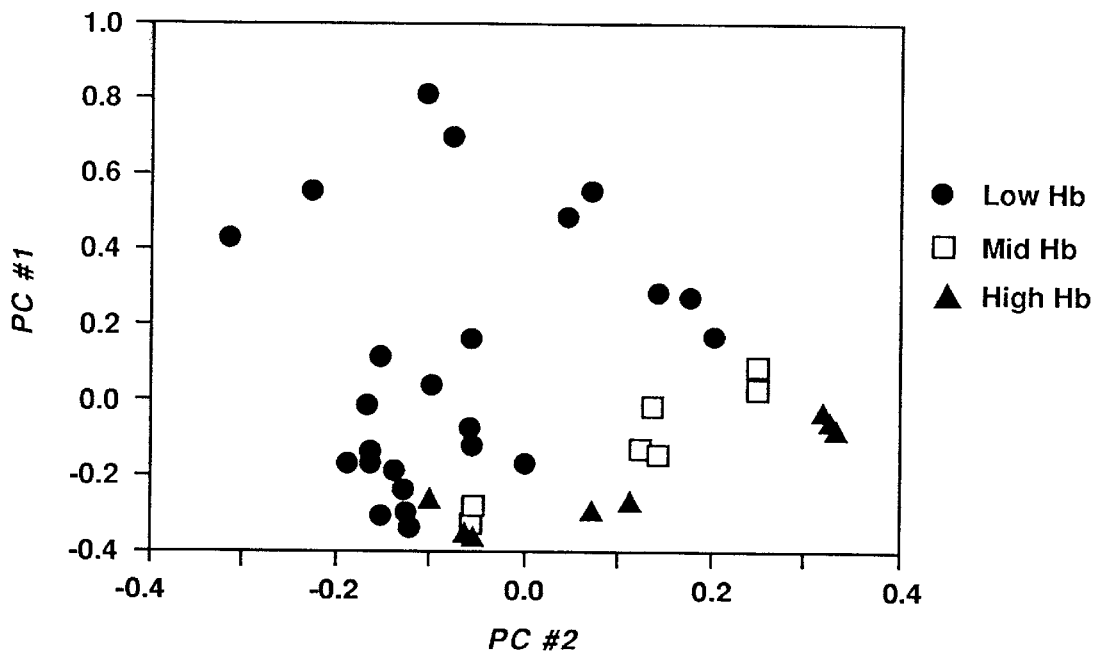
FIGS. 8 and 9 illustrate two dimensional projections of the test solutions of Example 2 on the first two principal components to determine if the test solutions cluster according to their concentration of hemoglobin.
Figure 9:
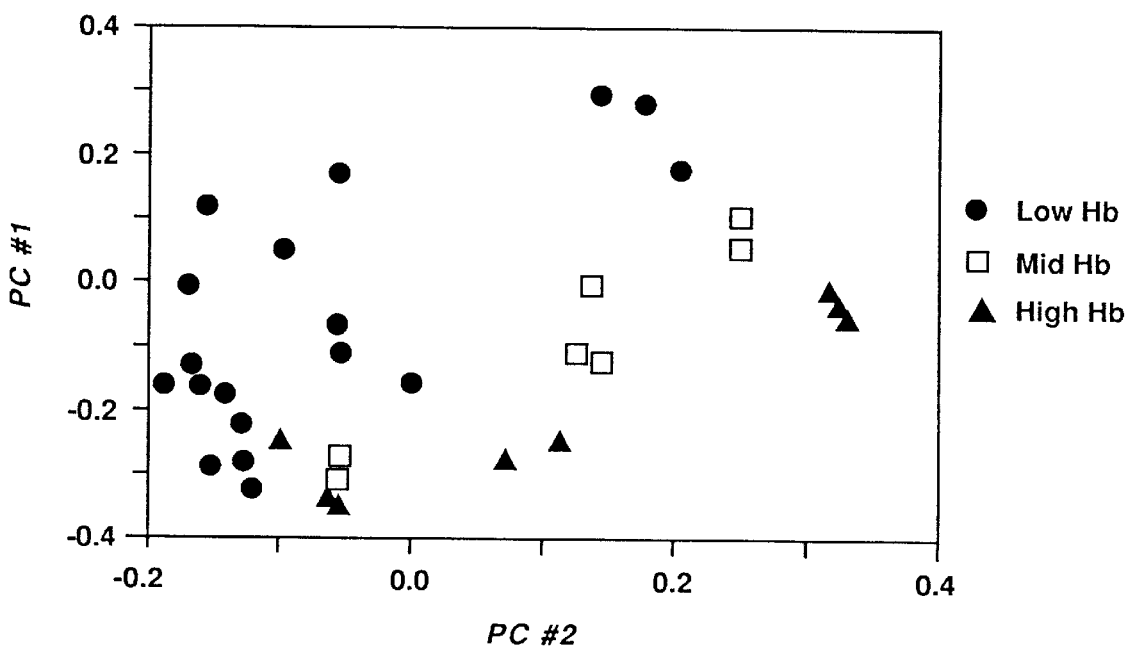

The amount of hemoglobin in the test solutions varied from 10 μg/ml to 1000 μg/ml. This range of concentrations was divided into three categories: low concentrations (less than 300 μg/ml), intermediate concentrations (300 μg/ml to 600 μg/ml), and high concentrations (greater than 600 μg/ml). PCA was performed on the 40×5 matrix R containing the responses from the plurality of sensor probes to each of the test solutions. Two dimensional projections of sensor probe responses to the test solutions on various principal components were examined to see if the test solutions were clustered according to the amount of hemoglobin they contained. In these plots, the axes are the principal components and the coordinates of the test solutions are the scores. PCA was successful at classifying the test solutions based on amount of hemoglobin they contained, as shown in FIG. 8. The clusters were less discrete than those for fibrinogen, but became more apparent when the lower right hand portion of FIG. 8 was expanded, as shown in FIG. 9. The fact that test solutions could be classified according to their hemoglobin concentrations using data from an anti-fibrinogen assay represents a significant improvement over the current art and illustrates the power and significance of the present invention.

Test solutions could not be successfully classified according to their albumin concentrations, at least by looking at two dimensional scores projection plots. Plotting the scores in three dimensions may provide resolution of test solutions based on their albumin concentrations and increased cluster separation for test solutions based on their hemoglobin concentrations.

The implications for clinical analysis are clear. Using a set of calibration test solutions and the responses from the plurality of sensor probes to these calibration test solutions, PCA defines regions in space that correspond to physiological conditions such as diabetes, pregnancy, or AIDS. Clinical test solutions are then analyzed by the plurality of sensor probes. The n×k matrix R* containing test solutions and sensor probe responses, where n is the number of test solutions and k is the number of sensor probes in the plurality of sensor probes, is projected onto the axes defined by the PCA model:

$$A^* = R^* Z \qquad \text{Eq. 29}$$

where Z is a k×c matrix of column loadings vectors determined in the calibration step and A* is the n×c matrix of newly calculated scores. Only these principal components which have been found to have the ability to classify samples are retained in the Z matrix. The newly calculated scores for each clinical test solution are plotted in two dimensional scores vs. scores plots like FIG. 7. For example, a test solution falling in the region of space previously determined to correspond to diabetes allows a diagnosis of diabetes to be made.

EXAMPLE 6

This example illustrates the selection of optimal partially selective surfaces using PLS model parameters with the data from Example 2. The above analysis in Examples 3–5 showed that a plurality of sensor probes linked with multivariate analysis represented a significant improvement over the current art. It is desirable to increase the prediction accuracy of the model for hemoglobin and albumin. The X-block loadings given by the PLS model suggested one method for further optimizing the plurality of sensor probes. It was previously demonstrated that for the first latent variable, the loadings for the untreated sensor probe (UN), the acetone plasma-deposited film sensor probe (ACE), the methane plasma-deposited film sensor probe (MTH), and the tetrafluoroethylene plasma-deposited film sensor probe (TFE) were almost identical, while the allylamine plasma-deposited film sensor probe (ALAM) was loaded less strongly.

Figure 10:
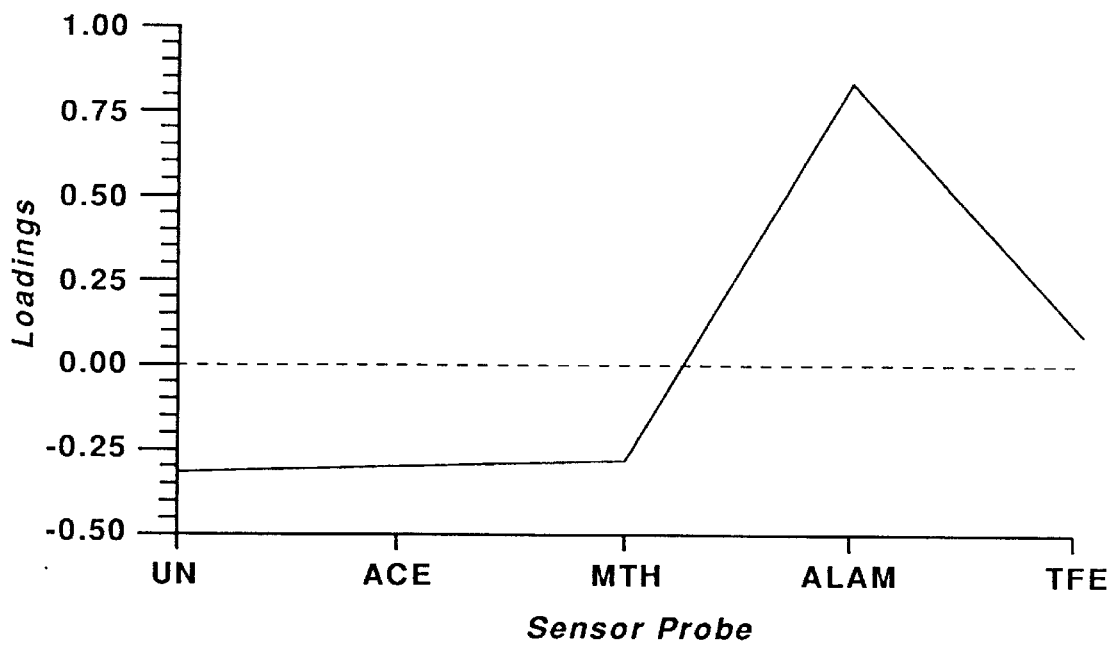
FIG. 10 shows the X-block loadings for the second latent variable according to the data in Example 2.

FIG. 10 shows the X-block loadings for the second latent variable. It can be seen that the responses from the UN, ACE, and MTH sensor probes were again loaded nearly equally, while the ALAM and TFE loadings were much different. Thus, for the first two latent variables, the UN, ACE, and MTH loadings were almost the same. This indicated that redundant or nearly redundant information was being contributed by these three sensor probes to the latent variables. In effect, the X-block consisted of only three significantly different sensor probes when using the first two latent variables.

Figure 11:
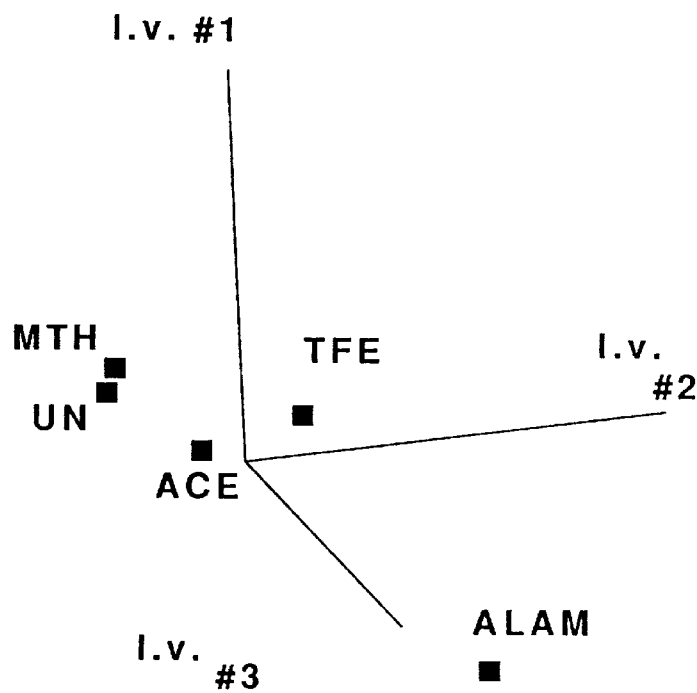
FIG. 11 is a three dimension plot of the loadings for the five sensor probes of Example 2 using the first three latent variables as axes. The origin has been shifted based on the variance of the plotted data, but the spatial relationship of the points is unchanged. The UN and MTH sensor probes appear close together, suggesting redundancy in the information these sensor probes supplied to the calibration and prediction PLS modeling process, even when three latent variables were used. The ACE, ALAM, and TFE sensor probes are more separate in space, suggesting that these sensor probes supply non-redundant information to the calibration and prediction PLS modeling process.

FIG. 11 is a three dimension plot of the loadings for the first sensor probes, using the first three latent variables as axes. The origin has been shifted based on the variance of the plotted data, but the spatial relationship of the points is unchanged. The UN and MTH sensor probes appear close together, suggesting redundancy in the information these sensor probes supplied to the calibration and prediction PLS modeling process even when three latent variables were used. The ACE, ALAM, and TFE sensor probes are more separate in space, suggesting that these sensor probes supplied nonredundant information to the calibration and prediction PLS modeling process.

After the loading plots suggested redundancy in the data from the UN and MTH sensor probes, the sensor probe responses from the plurality of sensor probes were further analyzed. Table 7 shows that the PLS model had pointed out a subtle characteristic of the actual data. Each column of Table 7 represents the average change in sensor probe response for the various sensor probes resulting from an incremental change in the concentration of the given protein, keeping constant the concentrations of the other two proteins. The step change in the fibrinogen concentrations was a 5× increase, while the step changes for albumin and hemoglobin were 10× increases.

TABLE 7

Pertubation of Sensor Response Resulting from an Increase in the Concentration of One Protein

| Sensor Probe | Protein Increased and Amount of Change (%) | | |
|---|---|---|---|
| | Fb (5x) | Ab (10x) | Hb (10x) |
| UN | 218.5 | 38.7 | 67.6 |
| MTH | 210.4 | 44.5 | 66.5 |
| ACE | 167.9 | 24.0 | 55.7 |
| TFE | 149.8 | 8.5 | 31.9 |
| ALAM | 264.8 | 16.4 | 119.0 |

It can be seen that the information from the UN and MTH sensor probes was indeed redundant. This was not apparent by merely looking at the data sets, for the numerical responses from these two sensor probes were significantly different. However, the relative changes in the sensor probe responses caused by alterations in the test solutions were nearly identical. The ACE sensor probe gave similar, but definitely different responses. The TFE and ALAM sensor probes were shown to be the most different in their responses.

Thus, the data set forth in the examples demonstrate that multivariate analysis clearly provided a powerful means of analyzing the sensor probe responses from the plurality of sensor probes. In addition, multivariate analysis provided information useful to the selection of appropriate partially selective surfaces for the construction and selection of surfaces for a more optimal plurality of sensor probes. Based on FIG. 11, the predictive ability of the PLS models built from sensor responses from the plurality of sensor probes can be enhanced by replacing either the UN or MTH sensor probes with a sensor probe that would provide unique information to the calibration and prediction process. Sensor probes with plasma-deposited films of plasma polymerized monomers containing phosphorous (i.e., $PH_3$/methane), chlorine (i.e., 1-Cholorbutane), silicon, or organometallics are good candidates to replace either the UN or the MTH sensor probes or use in addition to the existing sensor probes.

EXAMPLE 7

Figure 12A:
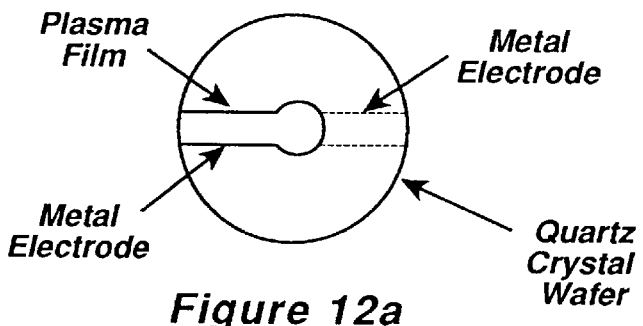
FIGS. 12(a–c), 13(a–b), 14(a–c), 15(a–b), 16(a–b), 17(a–b) and 18 illustrate various configurations of plurality of sensor probes using various detection devices.
Figure 12B:
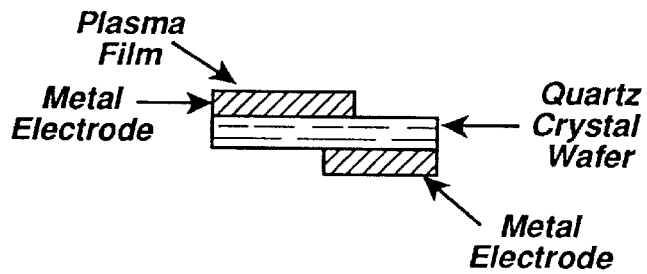
Figure 12C:
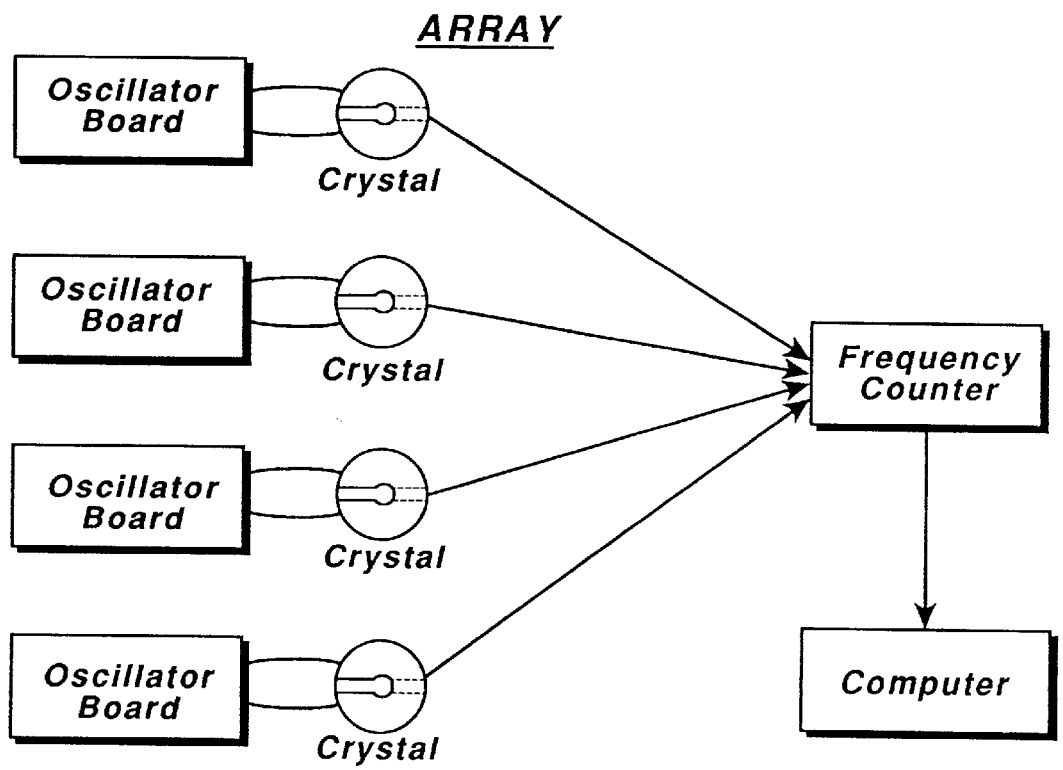

This example illustrates a plurality of sensor probes constructed with bulk acoustic wave devices. A schematic drawing of this embodiment is shown in FIG. 12 (FIGS. 12a, 12b, and 12c). Each bulk acoustic wave device comprises a substrate material that allows transmission of a voltage signal and a partially selective surface. Each substrate is an 0.5 inch diameter AT-cut quartz crystal wafer.

When voltage is applied across each quartz crystal wafer, the quartz crystal wafer oscillates at a characteristic frequency of 10 MHz.

The partially selective surfaces are comprised of vapor-deposited metal (similar to metal sputtering) electrodes of different metals deposited on opposite sides of the quartz crystal wafers. Some of the vapor deposited metal electrodes are covered with a plasma-deposited film produced by the plasma polymerization of various monomers.

The signal-generating device is a series of circuit boards that supplies each sensor probe with a voltage that causes the sensor probe to oscillate at its characteristic frequency of 10 MHz. The signal collection device is a frequency counter. The frequency counter is connected to a computer to which the frequency information is transferred, stored, and analyzed.

The plurality of sensor probes is contacted with a biological fluid containing proteins which bind to the partially selective surfaces via multiple noncovalent interactions. Each of the sensor probes adsorbs a unique protein layer as a result of its unique partially selective surface by multiple noncovalent interactions. The characteristic oscillation frequency of each sensor probe is perturbed uniquely by the proteins binding to the partially selective surface on each sensor probe. The changing oscillation frequency of each sensor probe is collected by the frequency counter as protein adsorption occurs. The resulting data set is the change in oscillation frequency for each sensor probe in the plurality of sensor probes for each time point at which the oscillation frequency of each sensor probe is recorded. These data form a multivariate data set which can be fully analyzed only by using multivariate statistics.

The sensing device is used as a biomedical analyte sensor, using multivariate statistics, to relate variations in the multivariate data set to the concentrations of certain biomedical analytes of interest, such as albumin, glucose, and potassium ions. The sensing device can also be used as a diagnostic sensor device, using multivariate statistics to relate variations in the multivariate data set to physiological conditions of interest, such as diabetes, pregnancy, or AIDS.

EXAMPLE 8

Figure 13A:
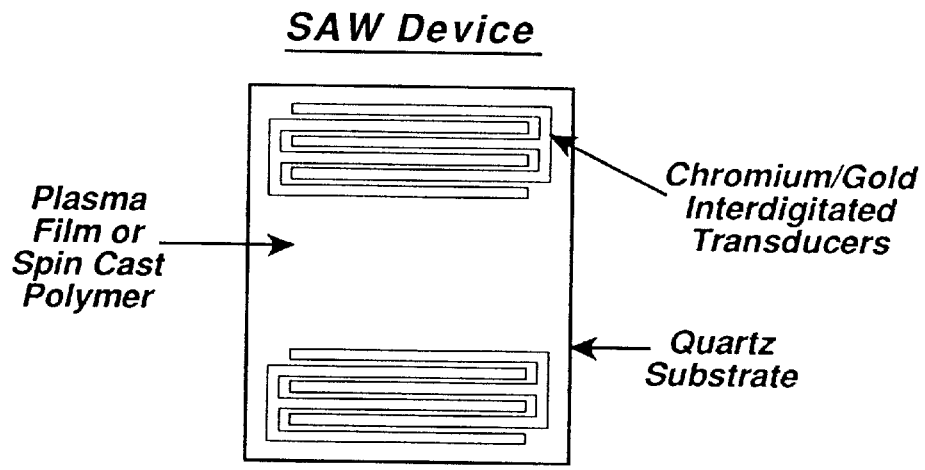
Figure 13B:
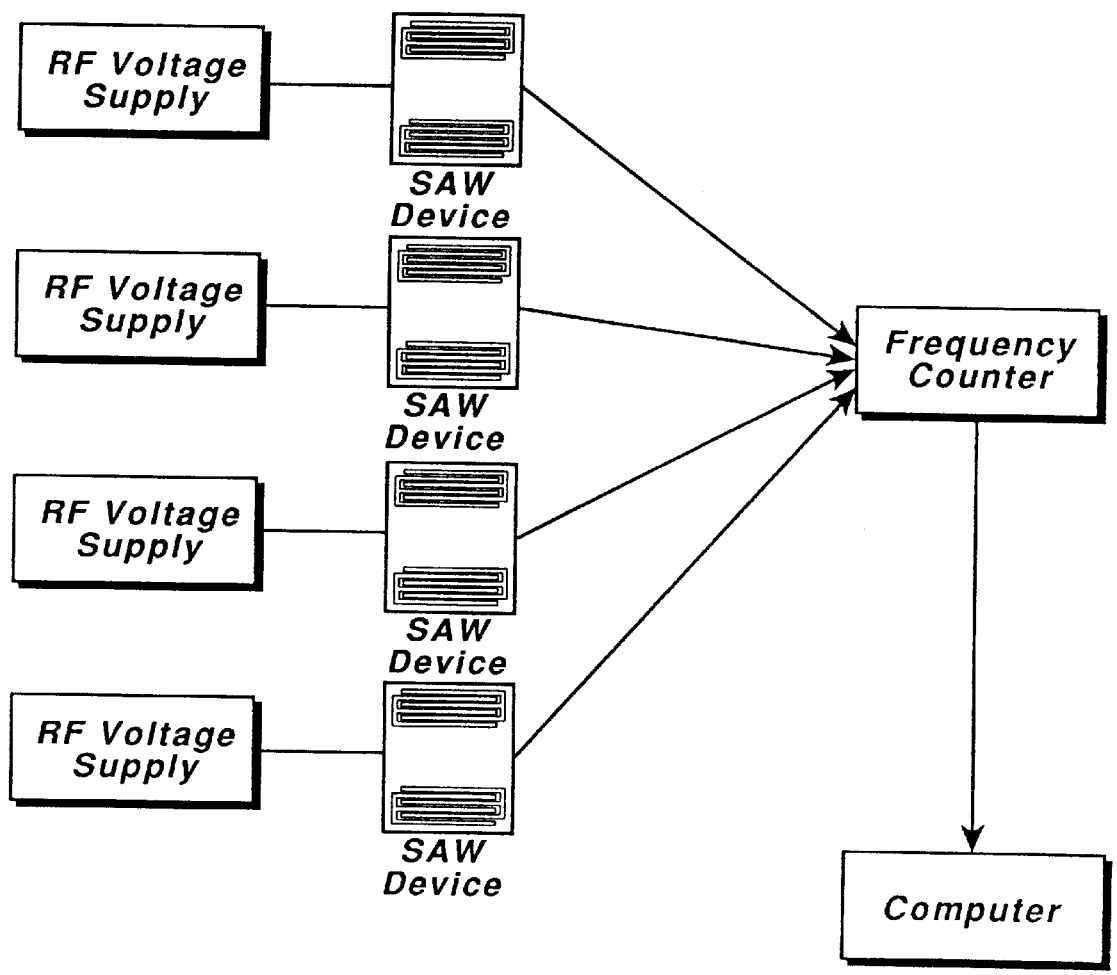

This example illustrates a plurality of sensor probes constructed using surface acoustic wave (SAW) devices. FIGS. 13a and 13b illustrate the embodiment of this multiple-probe sensor. Each sensor probe is comprised of a substrate, a ST-cut quartz wafer, with two sets of interdigitated transducers on top of the wafer. The interdigitated transducers, as shown in a close-up in FIG. 13, are overlapping fingers of layered metal (a layer of gold on top of a layer of chromium). The spacing between each finger is 16 microns and the width of each finger is 16 microns. There are 50 finger pairs in each set of interdigitated transducers. The first set of chromium/gold interdigitated transducers is at one edge of the quartz wafer, and the second set of chromium/gold interdigitated transducers is at the other edge of the quartz wafer.

The partially selective surfaces are plasma-deposited films from the plasma polymerization of various monomers deposited on top of the quartz wafers and chromium/gold interdigitated transducers. Additional partially selective surfaces comprise spin-cast polymers deposited on top of the quartz wafers and chromium/gold interdigitated transducers.

The signal-generating device is a power generator operating at radio frequencies that supplies voltage to the first set of chromium/gold interdigitated transducers. This voltage travels across the quartz wafer in the form of a wave of quartz molecules oscillating at a characteristic frequency of approximately 159 MHz. The wave is received at the second set of chromium/gold interdigitated transducers which transmits the signal carried by the wave to a signal-collection device. The signal-collection device is a frequency counter. The frequency counter is connected to a computer wherein the frequency information is transferred, stored, and analyzed.

The plurality of sensor probes is contacted with a biological fluid containing proteins which bind to the partially selective surfaces via multiple noncovalent interactions. Each of the sensor probes adsorbs a unique protein layer by multiple noncovalent interactions. The oscillation frequency of each sensor probe is perturbed uniquely by the proteins binding to the partially selective surface on the sensor probe.

The changing oscillation frequency of each sensor probe is collected by the frequency counter as the protein adsorption occurs. The resulting data set is the change in oscillation frequency for each sensor in the plurality of sensor probes for each time point at which the oscillation frequency of each sensor probe is recorded. This is a multivariate data set which can be fully analyzed only by using multivariate statistics.

The sensing device can also be used as a biomedical analyte sensor which uses multivariate statistics as is described in Example 7 herein.

EXAMPLE 9

Figure 14A:
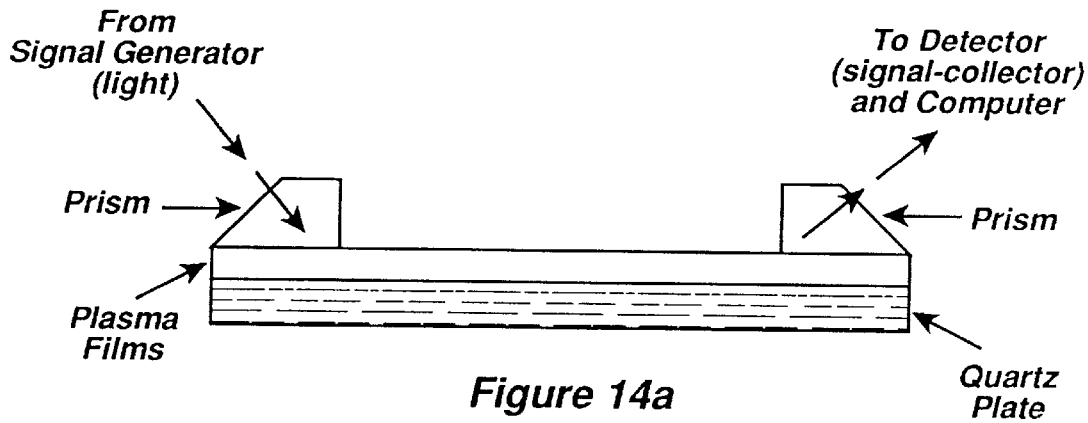

This example illustrates a multiple-probe sensor device constructed using prism coupling of near-infrared radiation into thin films of partially selective surfaces. This embodiment is illustrated in the side view (14a) and top view (14c) of FIG. 14. The partially selective surfaces are plasma deposited films from plasma polymerizable monomers deposited in strips lengthwise on a quartz plate base. Here, the substrate material forms the partially selective surface. The quartz base does not transmit signal and is not part of the substrate. Each sensor probe comprises a lengthwise strip of the quartz plate and a distinct region on the surface of this strip having a unique plasma-deposited film.

After the partially selective surfaces are deposited on each region of the quartz plate base, two SF 6 glass prisms are attached to the quartz plate base. One prism is at each end of the quartz plate base. The signal-generating device is a near-infrared spectrometer generating near-infrared radiation of various wavelengths in the near-infrared region of the electromagnetic spectrum.

The range of wavelengths in the near-infrared region of the electromagnetic spectrum is 0.7 to 2.4 microns. The signal-generating device scans through the near-infrared region of the electromagnetic spectrum, starting at the shorter wavelengths of the near-infrared region and generating successively longer wavelengths. The radiation is transmitted into the first prism, then is coupled from the prism into the distinct regions of the partially selective surfaces deposited on the surface of the quartz plate base. The near-infrared radiation travels across the partially selective surfaces deposited of the quartz plate base, propagating only in the partially selective surfaces. At the far end of the quartz plate, the near-infrared radiation leaves the partially selective surfaces as it is coupled into the second prism, which directs the near-infrared radiation to a signal-collection device. The signal-collection device is a photosensitive lead sulfide detector which detects the intensity of the collected near-infrared radiation at each wavelength. The lead sulfide detector is connected to a computer to which the intensity information is transferred and stored.

The plurality of sensor probes is contacted with a biological fluid containing proteins which bind to the partially selective surfaces via multiple noncovalent interactions. As the near-infrared radiation of increasing wavelengths travels through each partially selective surface, it interacts with a protein layer that is binding to the partially selective surface. Each of the sensor probes adsorbs a unique protein layer by multiple noncovalent interactions. The near-infrared radiation traveling through each partially selective surface is perturbed uniquely by the proteins binding to the partially selective surface on each sensor probe. The perturbed near-infrared radiation leaving each sensor probe is collected by the lead sulfide detector (one detector is enough for all of the probes) as the protein absorption occurs. The resulting data set is the intensity of the near-infrared radiation at each wavelength for each sensor in the plurality of sensor probes for each time period in which the near-infrared radiation was collected.

Similar sensing devices are constructed using a signal-generating device that generates far-infrared radiation at increasing wavelengths and a signal-collection device that is sensitive to far-infrared radiation, but is otherwise similar to the device described herein using near-infrared radiation. The range of wavelengths in the far-infrared region of the electromagnetic spectrum is 14.3 to 50 microns. Other sensing devices are constructed using a signal-generating device that generates mid-infrared radiation at increasing wavelengths and a signal-collection device that is sensitive to mid-infrared radiation, but is otherwise similar to the near-infrared device or the far-infrared device described herein. The range of wavelengths in the mid-infrared region of the electromagnetic spectrum is 2.4 to 14.3 microns. Still further sensing devices are constructed using a signal-generating device that generates visible radiation at increasing wavelengths and a signal-collection device that is sensitive to visible radiation, but is otherwise similar to the device described herein. The range of wavelengths in the visible region of the electromagnetic spectrum is 0.4 to 0.7 microns. Sensing devices are constructed using a single generating device that generates ultraviolet radiation and a signal collection device sensitive to ultraviolet radiation, but is otherwise similar to the device described herein. The range of wavelengths in the ultraviolet region of the electromagnetic spectrum is 0.2 to 0.4 microns. All of the near-infrared, mid-infrared, visible, and ultraviolet sensing devices operate much like the device described in this example.

EXAMPLE 10

Figure 14B:
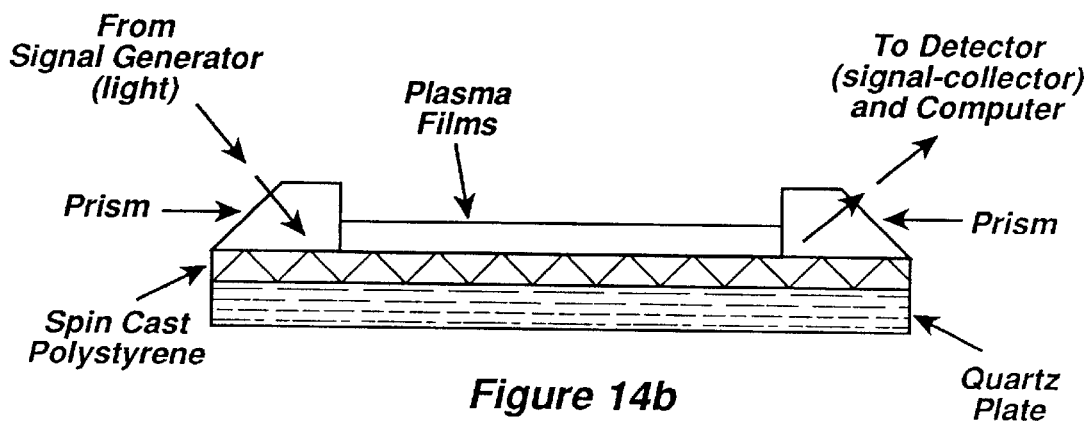
Figure 14C:
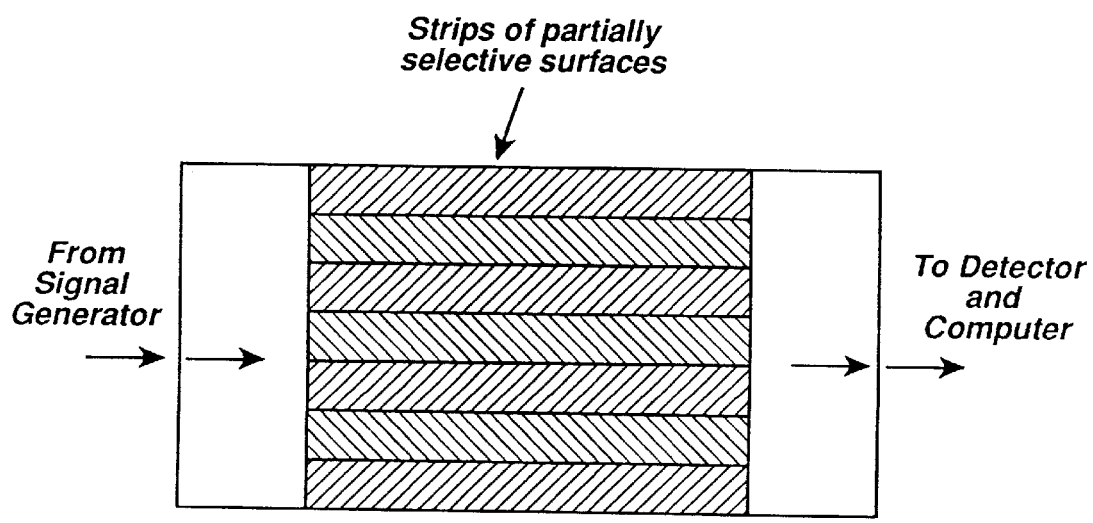

This example illustrates a thin film waveguide with a polystyrene film as a waveguide. The plurality of sensor probes is constructed using prism coupling of near-infrared radiation into a film of spin-cast polystyrene upon which a series of partially selective surfaces has been deposited. This embodiment is illustrated in FIG. 14b and the spin-cast polystyrene coats the quartz plate.

The near-infrared radiation travels across the surface of the polystyrene-coated quartz plate, propagating in the spin-cast polystyrene film. At the far end of the polystyrene-coated quartz plate, the near-infrared radiation is coupled from the spin-cast polystyrene film into the second prism, which directs the near-infrared radiation to a signal-collection device. The signal-collection device is a photosensitive lead sulfide detector which detects the intensity of the collected near-infrared radiation at each wavelength. The lead sulfide detector is connected to a computer in which the intensity information is transferred, stored, and analyzed.

As the near-infrared radiation travels through the spin-cast polystyrene film, it interacts with the partially selective surfaces and protein layer that is binding to the partially selective surfaces. Each of the sensor probes adsorbs a unique protein layer by multiple noncovalent interactions. The near-infrared radiation traveling through the spin-cast polystyrene film beneath each partially selective surface is perturbed uniquely by the partially selective surface and the proteins binding to the partially selective surface. The near-infrared radiation emanating from each sensor probe is collected by a lead sulfide detector as the protein adsorption occurs. The resulting data set is the intensity of the near-infrared radiation at each wavelength for each sensor in the plurality of sensor probes for each time period in which the near-infrared radiation was collected.

Similar sensing devices can also be constructed using signal-generating devices that generate far-infrared radiation at increasing wavelengths, mid-infrared radiation, visible radiation, and ultraviolet radiation, and corresponding signal collection devices.

EXAMPLE 11

Figure 15A:
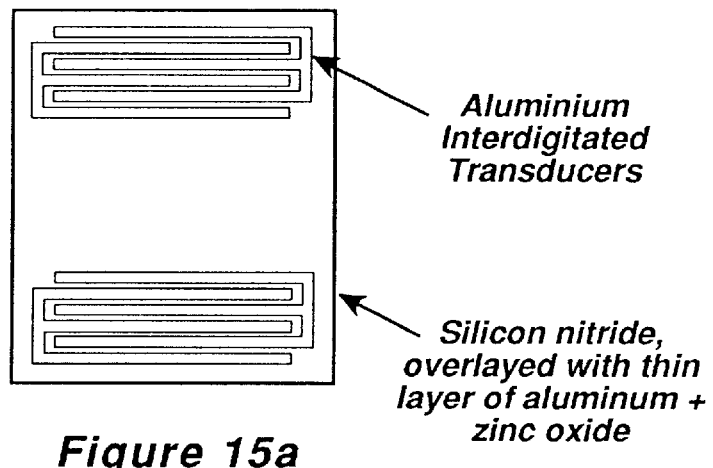
Figure 15B:
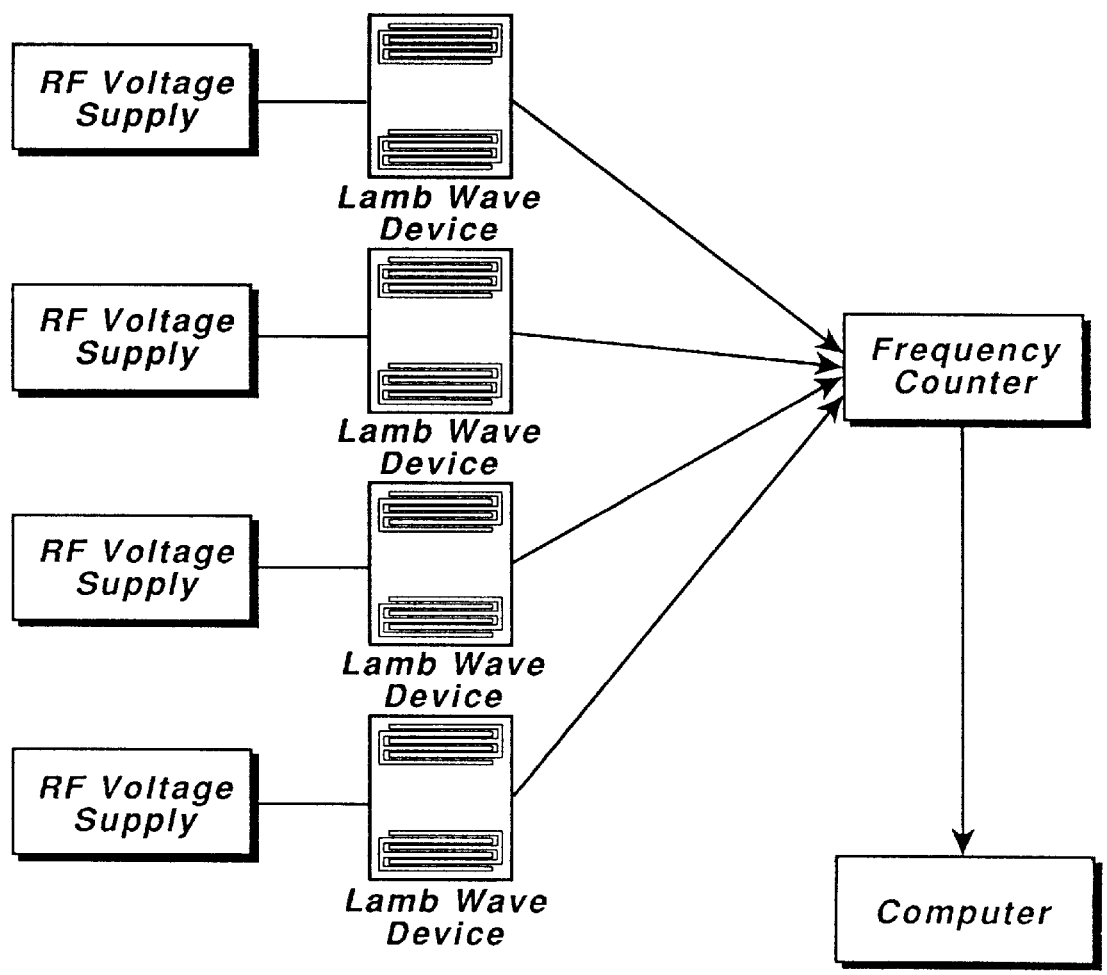

This example illustrates a plurality of sensor probes constructed using a plurality of Lamb-wave devices as shown in FIGS. 15a and 15b. Each sensor probe comprises a substrate material that allows the transmission of a voltage signal and a partially selective surface. Each substrate is a silicon nitride wafer with two sets of aluminum interdigitated transducers on the wafer. The interdigitated transducers are overlapping fingers of aluminum. The spacing between each finger pair is 100 microns. There are 25 finger pairs in each set of interdigitated transducers. Between the silicon nitride and the metal interdigitated transducers is a thin layer of aluminum and a thin layer of zinc oxide. The first set of aluminum interdigitated transducers is at one edge of the silicon nitride wafer, and the second set of aluminum interdigitated transducers is at the other edge of the silicon nitride wafer.

The partially selective surfaces comprise spin-cast polymers deposited on the silicon nitride wafers. The signal-generating device is a power source operating at radio frequencies that supplies a voltage to the first set of aluminum interdigitated transducers, causing the propagation of a Lamb wave at a characteristic oscillation frequency in the silicon nitride wafer. The wave is received at the second set of aluminum interdigitated transducers, which transmits the signal carried by the wave to a signal-collection device. The signal-collection device is a frequency counter which is connected to a computer to which the frequency information is transferred and stored.

A schematic diagram of this device is illustrated in FIG. 15. When the plurality of sensor probes, comprising the Lamb-wave devices with aluminum interdigitated transducers, is contacted with a biological fluid containing proteins which bind to the partially selective surfaces via multiple noncovalent interactions, the oscillation frequency of each sensor probe is perturbed uniquely by the proteins binding to the partially selective surface on the sensor probe. The changing oscillation frequency of each sensor probe is collected as protein adsorption occurs by the frequency counter. The resulting data set is the change in oscillation frequency for each sensor in the plurality of the sensor probes for each time point at which the oscillation frequency of each sensor probe is recorded. This is a multivariate data set.

EXAMPLE 12

Figure 16A:
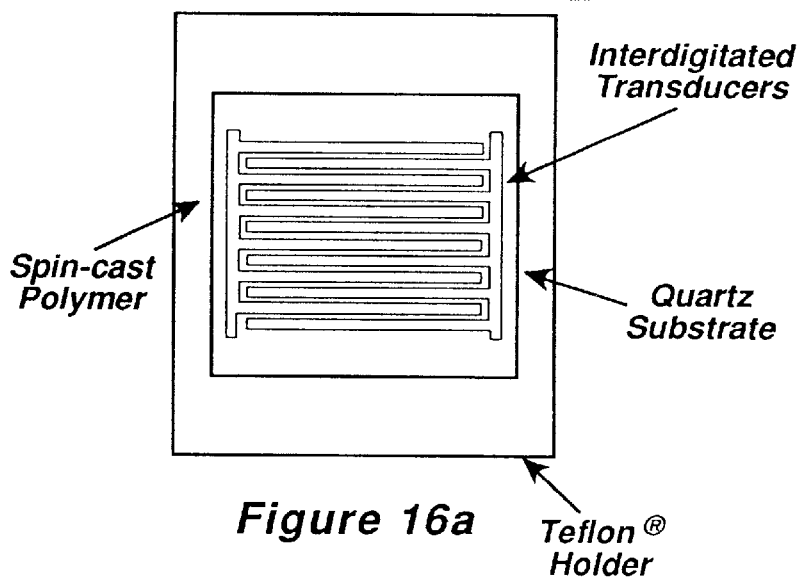
Figure 16B:
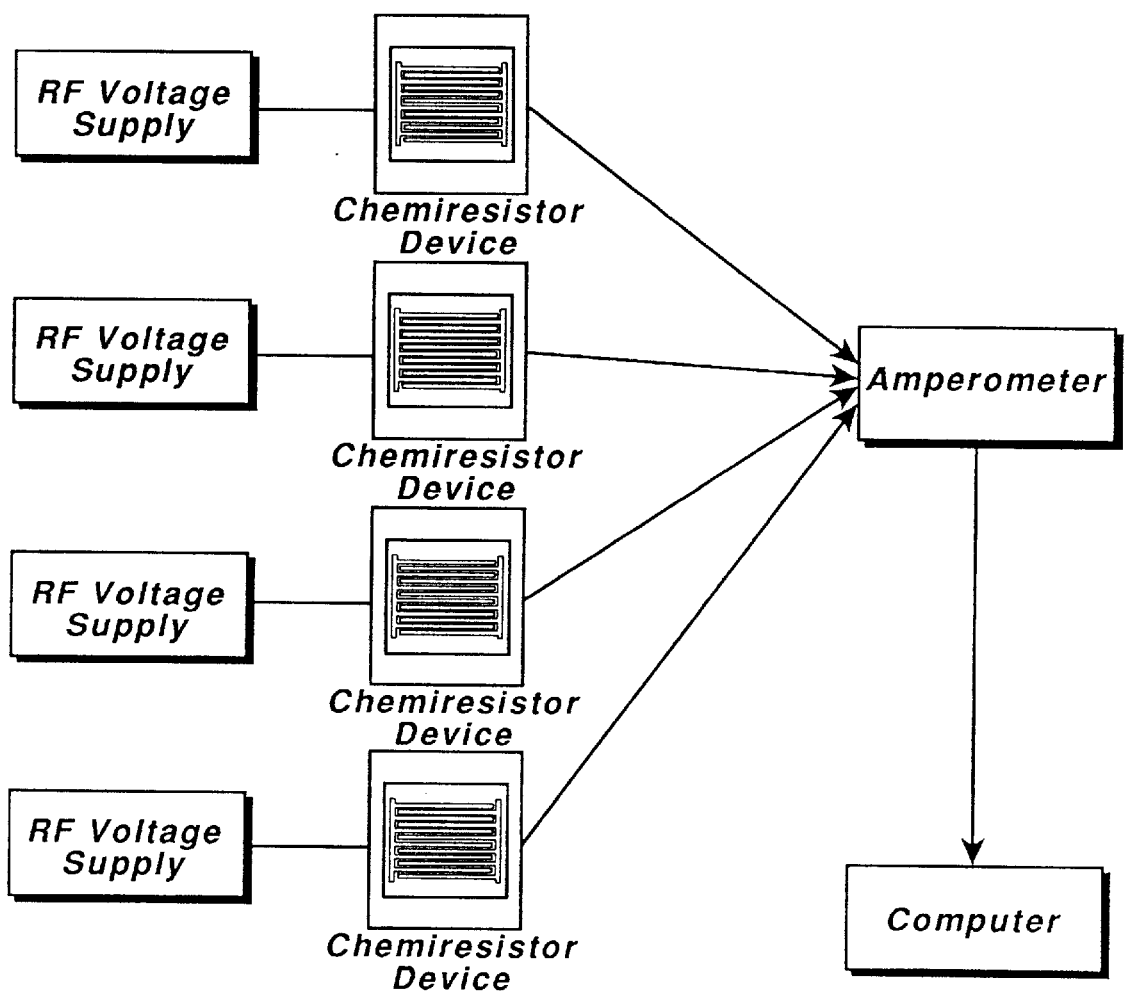

This example illustrates a plurality of sensor probes constructed using a plurality of chemiresistor devices as is illustrated in FIGS. 16a and 16b. Each substrate is a ST-cut quartz wafer with one set of metal interdigitated transducers on top of the wafer. The interdigitated transducers are overlapping fingers of gold. The spacing between each finger is 15 microns, and the width of each finger is 15 microns. There are 50 finger pairs in the set of interdigitated transducers. The partially selective surfaces comprise films of semiconducting spin-cast polymers deposited on top of the interdigitated transducers. The signal-generating device is a power source that supplies a small bias voltage to the interdigitated transducers, causing a current to pass through the sensor probe. The signal-collection device is an amperometer which is connected to a computer to which the current information is transferred and stored.

The plurality of sensor probes is contacted with a biological fluid containing proteins which bind to the partially selective surfaces via multiple noncovalent interactions. Each of the sensor probes adsorbs a unique protein layer by multiple noncovalent interactions. The current flowing through each sensor probe is perturbed uniquely by the protein layer binding to the partially selective surface on the sensor probe. The change in current in each sensor probe is collected as protein adsorption occurs by the amperometer. The resulting data set is the change in current for each sensor in the plurality of the sensor probes for each time point at which the current of each sensor probe is recorded. This is a multivariate data set. The sensing device can also be used as a biomedical analyte sensor.

EXAMPLE 13

This example illustrates the multiple probe sensor using fluorescence as the detection technique. Fluorescence is the emission of electromagnetic radiation by an emitting body caused by the influx of electromagnetic radiation into the emitting body. There is a range of wavelengths in the influx of electromagnetic radiation that will cause fluorescence to occur. The emitted radiation can also be of various wavelengths, but the maximum emitted energy intensity occurs at a certain characteristic wavelength. Fluorescent labels are often attached to biological molecules for measurement purposes as a substitute for radioactive labels. A common fluorescent label used in biological systems is fluorescein isothiocyanate (FITC). When excited by electromagnetic radiation with a wavelength of 492 nm, an FITC label emits electromagnetic radiation with a maximum at a wavelength of approximately 520 nm.

Figure 17A:
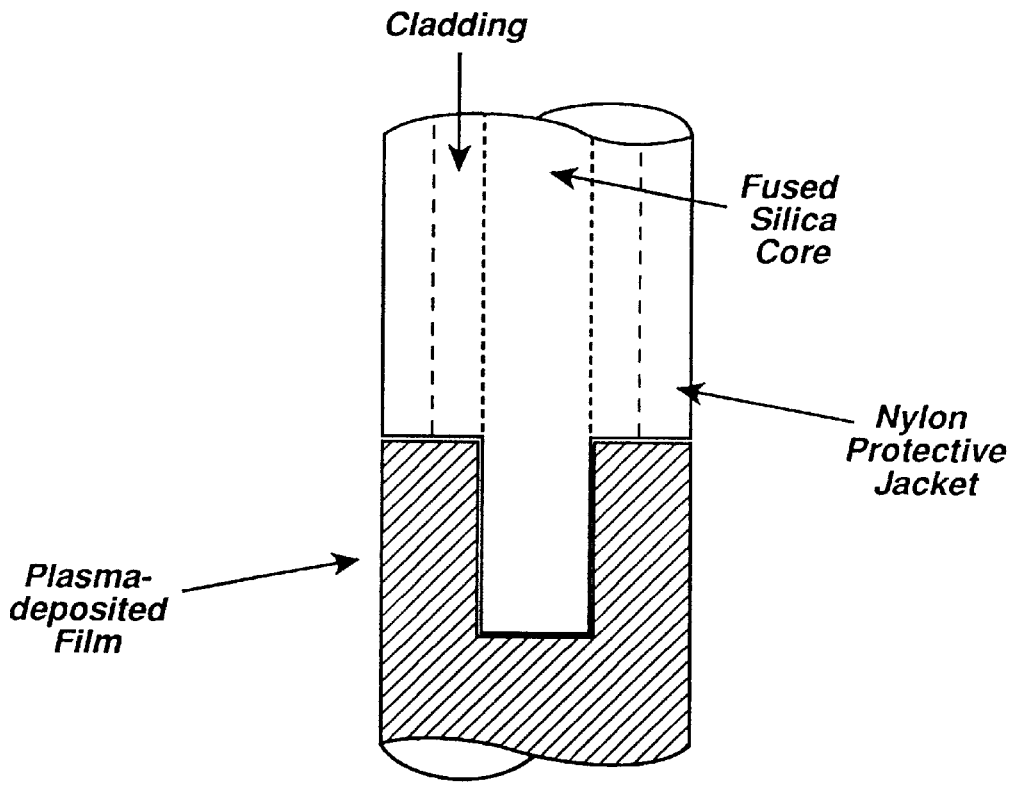
Figure 17B:
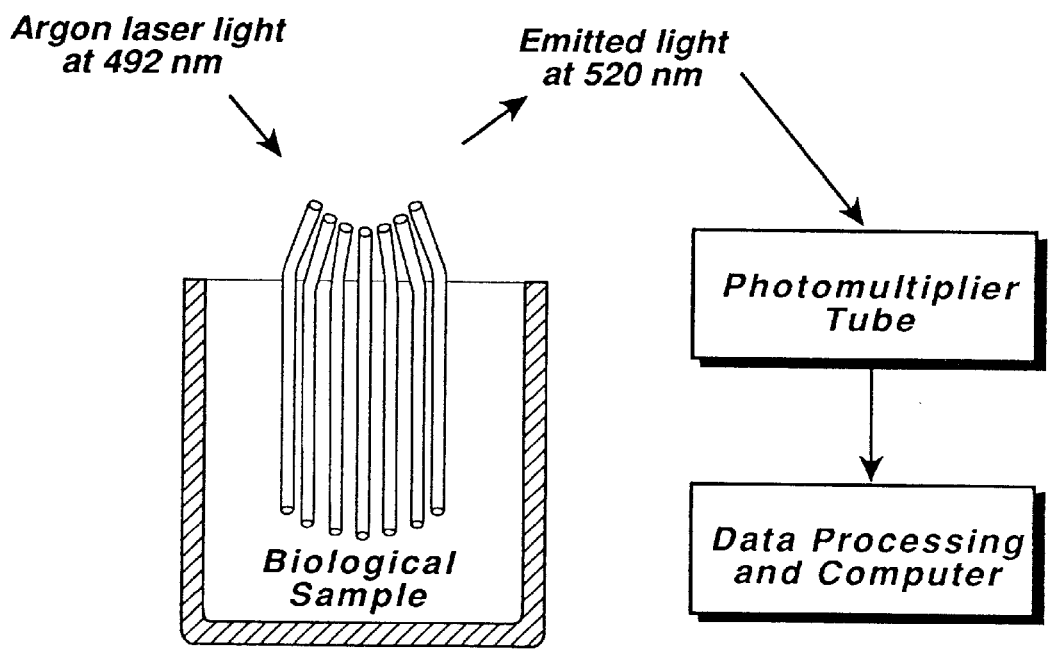

The plurality of sensor probes is constructed using a plurality of fiber optic cables as the substrate. This embodiment is shown in FIGS. 17a and 17b. Each fiber optic cable has a fused silica core 200 microns in diameter. The fused silica core is surrounded by a layer of silicone rubber cladding that is 100 microns thick. The silicone rubber cladding layer is surrounded by a protective jacket of nylon that is 100 microns thick. The substrate of each sensor probe is a fiber optic cable from which a length of the jacket and cladding sections have been removed using sulfuric acid, leaving exposed the glass core. The partially selective surfaces are different plasma-deposited films from the plasma polymerization of various monomers deposited on each fiber optic cable, especially in the region from which the jacket and cladding sections have been removed. At the end of each fiber optic cable is a dab of black wax. Each sensor probe comprises a different fiber optic cable with a different partially selective surface. The signal-generating device is an argon ion laser that has been tuned to produce light at a wavelength of 492 nm. The signal-collection device is a photomultiplier tube which is connected to a signal-processing device and a computer.

Before the sample of biological fluid to be tested is contacted with the plurality of sensor probes, a volume of fibrinogen labeled with FITC is added to the sample of biological fluid. The plurality of sensor probes is then dipped into the biological fluid and radiation from the signal-generating device is projected into the plurality of sensor probes. The sample of biological fluid contains proteins which bind to the partially selective surfaces via multiple noncovalent interactions. Each of the sensor probes adsorbs a unique protein layer by multiple noncovalent interactions. A unique fraction of fibrinogen labeled with FITC, which also adsorbs to the partially selective surfaces via multiple noncovalent interactions, will be present in each unique protein layer. The composition and structure of the adsorbed protein layers change with time as some adsorbed proteins rearrange and other adsorbed proteins are displaced from the partially selective surface and replaced by other proteins. The unique fraction of fibrinogen labeled with FITC in each unique protein layer will vary with time on each partially selective surface.

As the radiation from the signal-generating device impinges upon the fibrinogen with the FITC label, electromagnetic radiation with a maximum wavelength of 520 nm is emitted by the label. This emitted radiation is transmitted by the plurality of sensor probes and is then collected by the photomultiplier tube which measures the intensity of the radiation emitted from the unique protein layer adsorbed to the partially selective surface on each sensor probe as the protein adsorption occurs. The black wax at the end of each sensor probe absorbs the radiation from the signal-generating device that might otherwise be reflected back to the signal-collection device. The resulting data set is the intensity of the emitted radiation for each sensor in the plurality of the sensor probes for each time point at which the emitted radiation is collected. This is a multivariate data set. The sensing device can also be used a biomedical analyte sensor as described herein.

EXAMPLE 14

This example illustrates a plurality of sensor probes constructed using a plurality of glass slides upon which have been deposited plasma polymerized films from the plasma polymerization of various monomers. Each glass slide has a unique plasma polymerized film. The substrate of each sensor probe is the glass slide and the partially selective surface is the plasma polymerized film. The sensor probes are attached one at a time to a Wilhelmy balance. The Wilhelmy balance (CAHN) is a microbalance specially designed to record dynamic contact angles.

Figure 18:
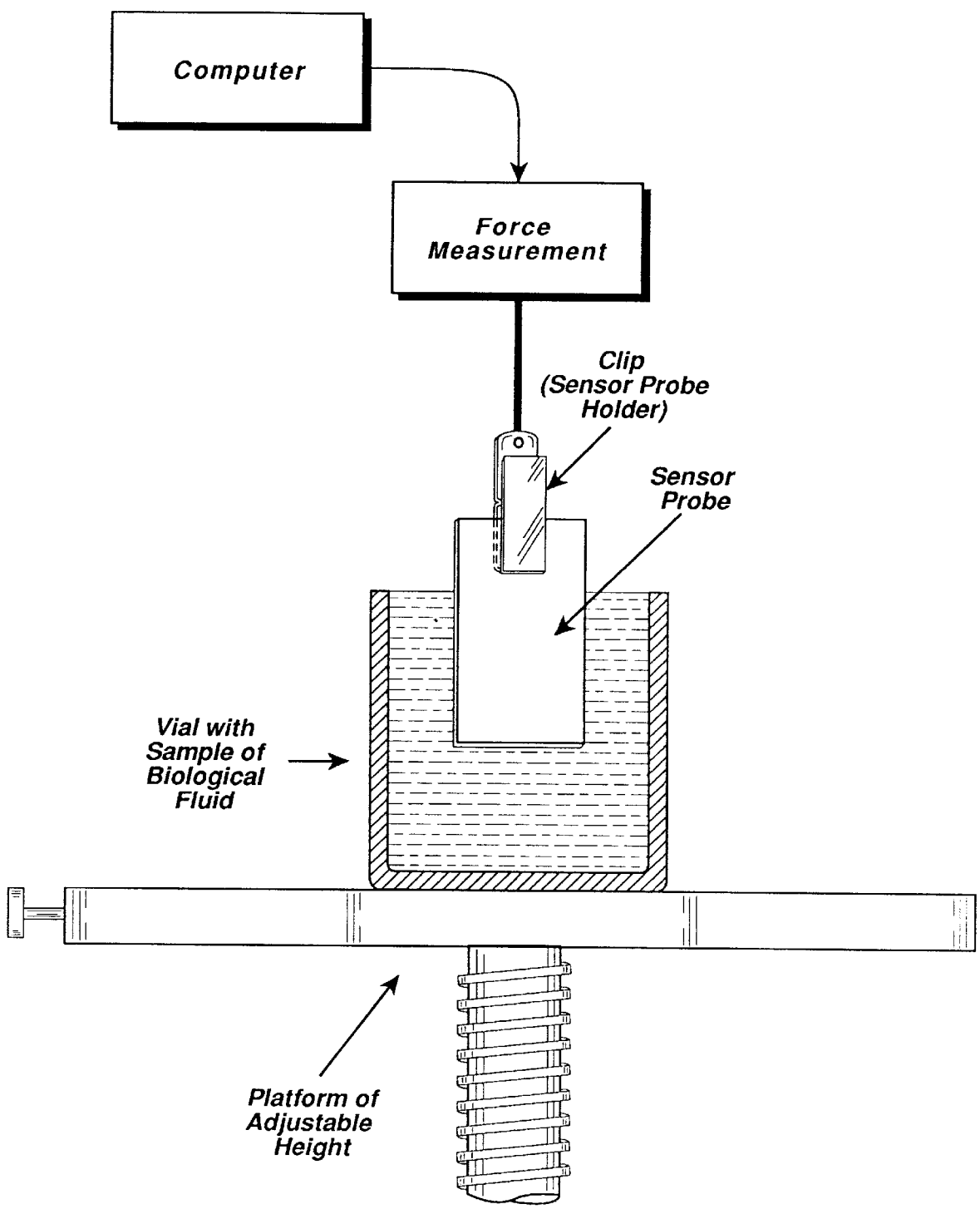

The main components of this example are illustrated in FIG. 18. The sensor probe is clipped to the sensor probe holder, which is connected by wire to a force measurement device (the signal-collection device). The force measurement device is connected to a computer to which the force information is transferred and stored. When the sensor probe is dipped into a biological fluid, the force measurement device measures the force that develops at the sensor probe/fluid/air interface. The sample of biological fluid is in a vial that is situated on a platform of adjustable height. This platform is the signal-generating device. As the platform moves up and down, the immersion depth of the sensor probe is altered, changing the force developed at the sensor probe/fluid/air interface. The data set collected is the force at each immersion depth measured as the immersion depth is increasing and the force at each immersion depth as the immersion depth is decreasing. After the data have been collected for one of the sensor probes, the sensor probe is removed from the sensor probe holder and a new sensor probe, possessing a unique partially selective surface, is attached. The data collection is repeated for this sensor probe and for the remainder of the plurality of sensor probes.

The resulting data set is the force at each sensor probe/fluid/air interface at each immersion depth as the immersion depth is increasing and the force at each immersion depth at the sensor probe/fluid/air interface when the immersion depth is decreasing for each sensor probe in the plurality of sensor probes for each immersion depth at which the force is recorded. This is a multivariate data set. The sensing device can also be used as a biomedical analyte sensor as described herein.

Although the foregoing invention has been described, in part, by way of illustration and example for the purposes of clarity and understanding, it will be apparent that certain changes or modifications may be practiced without deviating from the spirit and scope of the invention.

We claim:

1. A diagnostic sensor device comprising:
   a plurality of sensor probes in communication with at least one signal-generating device that generates a signal to the sensor probes, wherein each sensor probe comprises a substrate that allows for the transmission of the signal and a partially selective surface, wherein the partially selective surface binds proteins within a biological fluid through multiple, noncovalent and non-specific interactions, and wherein the partially selective surface of each sensor probe partitions the proteins within the biological fluid in a different manner;
   a means for detecting the signals, the detection means in communication with the plurality of sensor probes and detecting the signals after signal interaction with each partially selective surface; and
   a means for analyzing the signals from each partially selective surface by multivariate analysis, the analyzing means in communication with the detection means.

2. The diagnostic sensor device of claim 1 wherein the means for analyzing the signals from each partially selective surface is a computer with multivariate statistical analysis software.

3. The diagnostic sensor device of claim 1 wherein the partially selective surface is a plasma-polymerized film, a spin-coated polymer, a plasma-etched surface, or a metal-sputtered surface.

4. The diagnostic sensor device of claim 1 wherein the partially selective surface is a plasma-polymerized film of a polymerized monomer, wherein the monomer is selected from the group consisting of 2-mercaptoethanol, allylamine, allyl alcohol, acrylic acid, methane, benzene, tetrafluoroethane, methanol, acetone, chloroform, carbon tetrachloride, hexamethyldisilane, ethyl sulfide, ethyl chloroformate, 1,1,1,3,3,3,-Hexamethyldisilazane, acrylonitrile, trimethyldiborane, pyridine, tetramethylgermanium, 2-chloropropane, formic acid, ethylene oxide, ferrocene, diphenyl selenide, butanone, bromobenzene, trimethyl borate, tetrahydrofuran, chlorotrimethylsilane, hydroxyethylmethacrylate, vinyltrimethylsilane, dimethyl sulfoxide, hexafluorobenzene, perfluoropropane, allene, organometallics, and combinations thereof.

5. The diagnostic sensor of claim 1 wherein the partially selective surface is a plasma-etched surface produced by a plasma-etching gas, and wherein the plasma-etching gas is selected from the group consisting of argon, neon, nitrogen, air, helium, oxygen, fluorine, iodine, diborine, phosphine, krypton, sulfur dioxide, silicon (IV) chloride, and combinations thereof.

6. The diagnostic sensor device of claim 1 wherein the detection means is selected from the group consisting of infrared spectroscopy, UV spectroscopy, visible spectroscopy, surface acoustic wave devices, bulk acoustic wave devices, capacitance measurements, radioimmunoassay measurements, chemiluminescence measurements, Lamb-wave measurements, fluorescence measurements, Wilhelmy balance, chemiresistor measurements, electrochemical sensors, and enzyme-linked immunosorbent assay.

7. The diagnostic sensor device of claim 1 wherein at least one sensor probe further comprises a base, and wherein the substrate and the partially selective surface are the same and the substrate is supported by the base.

8. The diagnostic sensor device of claim 7 wherein the substrate and the partially selective surface are a thin film waveguide.

9. An analyte-measuring device for measuring an analyte or analytes in a biological fluid, comprising:

- a plurality of sensor probes in communication with at least one signal-generating device that generates a signal to the sensor probes, wherein each sensor probe comprises a substrate that allows for the transmission of the signal and a partially selective surface, wherein the partially selective surface binds proteins within the biological fluid through multiple, noncovalent and nonspecific interactions, with the proviso that the partially selective surface of each sensor probe partitions the proteins within the biological fluid in a different manner;
- a means for detecting the signals, the detection means in communication with the plurality of sensor probes and detecting the signals after signal interaction with each partially selective surface; and
- a means for analyzing the signals from each partially selective surface by multivariate analysis, the analyzing means in communication with the detection means.

10. The analyte-measuring device of claim 9 wherein the means for analyzing the signals from each partially selective surface is a computer with multivariate statistical analysis software.

11. The analyte-measuring device of claim 9 wherein the partially selective surface is a plasma-polymerized film, a spin-coated polymer, a plasma-etched surface, or a metal-sputtered surface.

12. The analyte-measuring device of claim 9 wherein the partially selective surface is a plasma-polymerized film of a polymerized monomer, wherein the monomer is selected from the group consisting of 2-mercaptoethanol, allylamine, allyl alcohol, acrylic acid, methane, benzene, tetrafluoroethane, methanol, acetone, chloroform, carbon tetrachloride, hexamethyldisilane, ethyl sulfide, ethyl chloroformate, 1,1,1,3,3,3,-Hexamethyldisilazane, trimethyldiborane, acrylonitrile, pyridine, tetramethylgermanium, 2-chloropropane, formic acid, ethylene oxide, ferrocene, diphenyl selenide, butanone, bromobenzene, trimethyl borate, tetrahydrofuran, chlorotrimethylsilane, hydroxyethylmethacrylate, vinyltrimethylsilane, dimethyl sulfoxide, hexafluorobenzene, perflouropropane, allene, organometallics, and combinations thereof.

13. The analyte-measuring device of claim 9 wherein the partially selective surface is a plasma-etched surface produced by a plasma-etching gas, and wherein the plasma-etching gas is selected from the group consisting of argon, neon, nitrogen, air, helium, oxygen, fluorine, iodine, diborine, phosphine, krypton, sulfur dioxide, silicon (IV) chloride, and combinations thereof.

14. The analyte-measuring device of claim 9 wherein the detection means is selected from the group consisting of infrared spectroscopy, UV spectroscopy, visible spectroscopy, surface acoustic wave devices, bulk acoustic wave devices, capacitance measurements, radioimmunoassay measurements, chemiluminescence measurements, Lamb-wave measurements, fluorescence measurements, Wilhelmy balance, chemiresistor measurements, electrochemical sensors, and enzyme-linked immunosorbent assay.

15. The analyte-measuring device of claim 9 wherein at least one sensor probe further comprises a base, and wherein the substrate and the partially selective surface are the same and the substrate is supported by the base.

16. The analyte-measuring device of claim 15 wherein the substrate and the partially selective surface are a thin film waveguide.

* * * * *